United States Patent
Banowski et al.

(10) Patent No.: US 8,828,367 B2
(45) Date of Patent: ***Sep. 9, 2014

(54) WATER-FREE ANTIPERSPIRANT NON-AEROSOLS IN WHICH ACTIVE SUBSTANCES ARE MORE READILY RELEASED

(75) Inventors: Bernhard Banowski, Dusseldorf (DE); Nadine Buse, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/417,470

(22) Filed: Mar. 12, 2012

(65) Prior Publication Data

US 2012/0177589 A1    Jul. 12, 2012

Related U.S. Application Data

(63) Continuation of application No. PCT/EP2010/063571, filed on Sep. 15, 2010.

(30) Foreign Application Priority Data

Sep. 22, 2009    (DE) .......................... 10 2009 029 671

(51) Int. Cl.
*A61K 8/00* (2006.01)
*A61K 8/26* (2006.01)
*A61K 8/86* (2006.01)

(52) U.S. Cl.
USPC ........................................ 424/65; 424/401

(58) Field of Classification Search
USPC ................................... 424/65, 401
See application file for complete search history.

(56) References Cited

U.S. PATENT DOCUMENTS

| | | | |
|---|---|---|---|
| 2,571,030 A | 10/1951 | Govett et al. | |
| 3,887,692 A | 6/1975 | Gilman | |
| 3,904,741 A | 9/1975 | Jones et al. | |
| 4,359,456 A | 11/1982 | Gosling et al. | |
| 4,479,887 A | 10/1984 | Seibert | |
| 4,775,528 A | 10/1988 | Callaghan et al. | |
| 5,017,360 A | 5/1991 | Katsoulis | |
| 5,080,830 A | 1/1992 | Damaso | |
| 5,118,497 A | 6/1992 | Katsoulis | |
| 5,643,558 A | 7/1997 | Provancal et al. | |
| 5,705,171 A | 1/1998 | Iovanni et al. | |
| 5,725,846 A | 3/1998 | Vu et al. | |
| 5,939,055 A | 8/1999 | Vu et al. | |
| 6,010,688 A | 1/2000 | Shen | |
| 6,042,816 A | 3/2000 | Shen | |
| 6,074,632 A | 6/2000 | Shen | |
| 6,245,325 B1 | 6/2001 | Shen | |
| 6,403,070 B1 * | 6/2002 | Pataut et al. | 424/65 |
| 6,613,338 B1 | 9/2003 | Schreiber et al. | |
| 6,663,854 B1 | 12/2003 | Shen et al. | |
| 6,838,032 B2 | 1/2005 | Grosz et al. | |
| 6,902,723 B2 | 6/2005 | Shen | |
| 6,936,242 B2 | 8/2005 | Elliott et al. | |
| 2001/0051138 A1 | 12/2001 | Scafidi et al. | |
| 2004/0009133 A1 | 1/2004 | Kolodzik et al. | |

FOREIGN PATENT DOCUMENTS

| | | |
|---|---|---|
| DE | 19501288 A1 | 7/1996 |
| DE | 19756454 C1 | 6/1999 |
| EP | 1269977 A2 | 1/2003 |
| EP | 0812183 B1 | 5/2003 |
| GB | 1347950 A | 2/1974 |
| GB | 2048229 A | 12/1980 |
| WO | WO 98/17238 A1 | 4/1998 |
| WO | WO 98/18441 A1 | 5/1998 |
| WO | WO 00/67712 A1 | 11/2000 |
| WO | WO 2009/083547 A2 | 7/2009 |
| WO | WO 2009/083807 A2 | 7/2009 |

OTHER PUBLICATIONS

Flick, E., Cosmetics Additives: An Industrial Guide, 1991, Noyes Publications, p. 6.*
PCT International Search Report (PCT/EP2010/063571) dated Feb. 21, 2011.

* cited by examiner

*Primary Examiner* — Gina C Justice
(74) *Attorney, Agent, or Firm* — David K. Benson

(57) ABSTRACT

Antiperspirant compositions for personal body care are produced as a non-aerosol, stick, soft solid, cream, gel, non-sprayable suspension, non-sprayable solution, or impregnated on a substrate and include at least one antiperspirant, at least one oil as a carrier, said oil being liquid in normal conditions, 0-7 percent by weight of free water relative to the weight of the composition, and at least one selected alkyl-modified polyether.

10 Claims, No Drawings

WATER-FREE ANTIPERSPIRANT NON-AEROSOLS IN WHICH ACTIVE SUBSTANCES ARE MORE READILY RELEASED

CROSS-REFERENCES TO RELATED APPLICATIONS

This application is a continuation of PCT/EP2010/063571, filed on Sep. 15, 2010, which claims priority under 35 U.S.C. §119 to DE 10 2009 029 671.9 filed on Sep. 22, 2009, both of which are hereby incorporated by reference.

FIELD OF THE INVENTION

The present invention generally relates to water-free antiperspirant compositions for personal body care, made up as a non-aerosol, stick, soft solid, cream, gel, non-sprayable suspension, non-sprayable solution or impregnated on a substrate, which allow improved active substance release of the active antiperspirant substance.

BACKGROUND OF THE INVENTION

Water-free antiperspirant compositions made up as a non-aerosol, stick, cream, gel, suspension or solution generally contain, in addition to the active sweat-reducing substances, at least one cosmetic oil as carrier for the particulate active sweat-reducing substance. So that the active antiperspirant substance suspended in the oil does not settle out during storage, commercial suspensions, gels, creams and sticks contain a suspending or thickening agent; in gels, e.g. hydrophobically modified hectorites as available, for example, with the trade name Bentone Gel from Rheox and Elementis Specialties, and in sticks, thickeners such as fatty alcohols and/or waxes.

In commercial water-free antiperspirant compositions, the active antiperspirant substance suspended in the water-free, oil-containing carrier is covered with an oil layer. However, this oil layer delays the release of the active antiperspirant substance in the effective water-soluble form.

In the prior art, water-containing antiperspirant creams with a water content of 43.9 wt. % are known from U.S. Pat. Nos. 5,118,497 and 5,017,360, which are emulsified with the aid of the commercial product Elfacos ST-37, an alkyl-modified polyether with the INCI name PEG-22/Dodecyl Glycol Copolymer, which has an HLB value of 2.4.

U.S. Pat. No. 6,613,338, and in particular WO 98/17238 A1, disclose sticks, in particular antiperspirant sticks, in the form of solid water-in-oil emulsions with a water content of 30-85 wt. %, which are emulsified with the aid of an alkyl-modified polyether of the general formula ACTIVATOR-(I) with the INCI name Methoxy PEG-22/Dodecyl Glycol Copolymer. This prior art gave the person skilled in the art no indication that alkyl-modified polyethers of the general formula ACTIVATOR-(I) can improve the release of the active antiperspirant substance from a water-free composition.

WO 2009/083547 A2 and WO 2009/083807 A2 teach that certain organosiloxane-oxyalkylene copolymers can improve the release of the active antiperspirant substance from a water-free composition. As a disadvantage of these substances, however, it has been shown that under certain circumstances, in particular when the cosmetic carrier contains little or no silicone oil, they are difficult to incorporate and to mix in homogeneously.

Desirable features and characteristics of the present invention will become apparent from the subsequent detailed description of the invention and the appended claims, taken in conjunction with this background of the invention.

BRIEF SUMMARY OF THE INVENTION

Surprisingly, it has now been found that the release of the active antiperspirant substance from a water-free antiperspirant composition can be improved if the composition includes at least one alkyl-modified polyether of the general formula ACTIVATOR-(I)

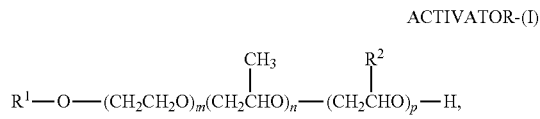

ACTIVATOR-(I)

wherein $R^1$ signifies an aliphatic hydrocarbon residue with 1 to 3 C atoms,
$R^2$ signifies an aliphatic hydrocarbon residue with 8 to 30 C atoms,
m is a rational number from 10 to 50,
n is a rational number from 0 to 10, and
p is a rational number from 1 to 10.

The present invention therefore provides antiperspirant compositions for personal body care made up as a non-aerosol, stick, soft solid, cream, gel, non-sprayable suspension, non-sprayable solution or impregnated on a substrate, containing at least one active antiperspirant substance, at least one oil which is liquid under normal conditions as carrier, 0-7 wt. %, preferably 0-3 wt. %, free water, based on the weight of the composition, and at least one alkyl-modified polyether of the general formula ACTIVATOR-(I).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The antiperspirant compositions according to the invention on a water-free basis are made up as a stick, soft solid, cream, gel, suspension, solution or as a substrate (wipe, pad, puff etc) impregnated with the composition.

All of the quantitative data provided below refer to the weight of the overall, ready-to-use composition.

"Normal conditions" within the meaning of the present application are a temperature of 20° C. and a pressure of 1013.25 mbar. Melting point data also refer to a pressure of 1013.25 mbar.

Preferred compositions according to the invention are characterized in that the alkyl-modified polyether d) is selected from compounds of the general formula ACTIVATOR-(I), wherein
$R^1$ is selected from a methyl group, an ethyl group, an n-propyl group and a 1-methylethyl group, preferably a methyl group,
$R^2$ is selected from an n-octyl, 2-ethylhexyl, n-nonyl, n-decyl, 2-ethyloctyl, n-undecyl, n-dodecyl, 2-ethyldecyl, n-tridecyl, myristyl, n-pentadecyl, cetyl, palmityl, stearyl, elaidyl, arachidyl, behenyl or cocyl group, preferably an n-decyl group,
m represents a rational number from 12-30, preferably 22-23, n represents a rational number from 0-8, preferably 0-4, particularly preferably 0, p represents a rational number from 1-9, preferably 4-8, particularly preferably 5-7.

Preferred for the teaching according to the invention (composition, use, method) are those alkyl-modified polyethers d) of the general formula ACTIVATOR-(I) in which $R^1$ represents a methyl group.

Also preferred for the teaching according to the invention (composition, use, method) are those alkyl-modified polyethers d) of the general formula ACTIVATOR-(I) in which $R^2$ represents an n-decyl group.

Also preferred for the teaching according to the invention (composition, use, method) are those alkyl-modified polyethers d) of the general formula ACTIVATOR-(I) in which m represents a rational number from 21-23.

Also preferred for the teaching according to the invention (composition, use, method) are those alkyl-modified polyethers d) of the general formula ACTIVATOR-(I) in which m represents a rational number from 22-23.

Also preferred for the teaching according to the invention (composition, use, method) are those alkyl-modified polyethers d) of the general formula ACTIVATOR-(I) in which n=0.

Also preferred for the teaching according to the invention (composition, use, method) are those alkyl-modified polyethers d) of the general formula ACTIVATOR-(I) in which p represents a rational number from 4-5.

Also preferred for the teaching according to the invention (composition, use, method) are those alkyl-modified polyethers d) of the general formula ACTIVATOR-(I) in which p represents a rational number from 6-8.

Also preferred for the teaching according to the invention (composition, use, method) are those alkyl-modified polyethers d) of the general formula ACTIVATOR-(I) in which p represents a rational number from 7-8.

Also preferred for the teaching according to the invention (composition, use, method) are those alkyl-modified polyethers d) of the general formula ACTIVATOR-(I) in which $R^1$ represents a methyl group, $R^2$ an n-decyl group, m a rational number from 22-23, n=0 and p represents a rational number from 4-5.

Also preferred for the teaching according to the invention (composition, use, method) are those alkyl-modified polyethers d) of the general formula ACTIVATOR-(I) in which $R^1$ represents a methyl group, $R^2$ an n-decyl group, m a rational number from 22-23, n=0 and p represents a rational number from 7-8.

Other preferred compositions according to the invention are characterized in that the alkyl-modified polyether d) of the general formula ACTIVATOR-(I), wherein $R^1$ is an aliphatic hydrocarbon residue with 1 to 3 C atoms, $R^2$ is an aliphatic hydrocarbon residue with 8 to 30 C atoms, m is a rational number from 10 to 50, n is a rational number from 0 to 10 and p is a rational number from 1 to 10, has an HLB value in the range of 5-7, preferably 6-6.8, particularly preferably 6.2-6.5.

Other preferred compositions according to the invention are characterized in that the alkyl-modified polyether d) of the general formula ACTIVATOR-(I), wherein $R^1$ is selected from a methyl group, an ethyl group, an n-propyl group and a 1-methylethyl group, preferably a methyl group, $R^2$ is selected from an n-octyl, 2-ethylhexyl, n-nonyl, n-decyl, 2-ethyloctyl, n-undecyl, n-dodecyl, 2-ethyldecyl, n-tridecyl, myristyl, n-pentadecyl, cetyl, palmityl, stearyl, elaidyl, arachidyl, behenyl or cocyl group, preferably an n-decyl group, m represents a rational number from 12-30, preferably 22-23, n represents a rational number from 0-8, preferably 0-4, particularly preferably 0, p represents a rational number from 1-9, preferably 4-8, particularly preferably 5-7, has an HLB value in the range of 5-7, preferably 6-6.8, particularly preferably 6.2-6.5.

Other preferred compositions according to the invention are characterized in that the alkyl-modified polyether d) of the general formula ACTIVATOR-(I) illustrated above, wherein $R^1$ is selected from a methyl group, $R^2$ is selected from an n-decyl group, m is a rational number from 22-23, n=0 and p is a rational number from 4-8, has an HLB value in the range of 5-7, preferably 6-6.8, particularly preferably 6.2-6.5.

Preferred alkyl-modified polyethers of the general formula ACTIVATOR-(I) according to the invention are obtainable by the production method disclosed in U.S. Pat. No. 4,479,887 according to Example 1, in particular Examples 1A and 1D, from a $C_1$-$C_3$ alkanol ethoxylate and a 1,2-epoxy-$C_{10}$-$C_{32}$ alkane. A preferred alkyl-modified polyether of the general formula ACTIVATOR-(I) according to the invention is selected from compounds with the INCI name Methoxy PEG-22/Dodecyl Glycol Copolymer. One compound of this type is available, for example, as the commercial product Elfacos E 200.

Other preferred compositions according to the invention are characterized in that at least one alkyl-modified polyether d) of the general formula ACTIVATOR-(I) illustrated above is contained in a total quantity of 0.01-5 wt. %, preferably 0.1-3 wt. %, particularly preferably in a total quantity of 0.5-2 wt. %, extraordinarily preferably in a total quantity of 1-1.5 wt. %, based in each case on the total weight of the composition.

Other preferred compositions according to the invention are characterized in that Methoxy PEG-22/Dodecyl Glycol Copolymer is contained in a total quantity of 0.01-5 wt. %, preferably 0.1-3 wt. %, particularly preferably in a total quantity of 0.5-2 wt. %, extraordinarily preferably in a total quantity of 1-1.5 wt. %, based in each case on the total weight of the composition.

Alkyl-modified polyethers d) of the general formula ACTIVATOR-(I) illustrated above can be readily incorporated and homogeneously mixed into the compositions according to the invention, even if the cosmetic carrier contains little or no silicone oil.

The compositions according to the invention are substantially water-free, i.e. they contain 0 to no more than 7 wt. %, preferably 0 to no more than 3 wt. % free water, extraordinarily preferably 0 to no more than 2 wt. %, of free water, based in each case on the overall composition. The content of water of crystallization, water of hydration or similarly molecularly bound water that can be contained in the components used, in particular in the active antiperspirant substances, does not represent free water within the meaning of the present application.

The compositions according to the invention contain at least one active antiperspirant substance.

Preferred active antiperspirant substances are selected from the water-soluble astringent inorganic and organic salts of aluminum and zinc or any mixtures of these salts.

Aluminosilicates and zeolites are not included in the active antiperspirant substances according to the invention.

According to the invention, water solubility is understood as a solubility of at least 5 wt. % at 20° C., i.e. quantities of at least 5 g of the active antiperspirant substance are soluble in 95 g water at 20° C.

Particularly preferred active antiperspirant substances are selected from aluminum chlorohydrate, in particular aluminum chlorohydrate with the general formula $[Al_2(OH)_5Cl.1\text{-}6\,H_2O]_n$, preferably $[Al_2(OH)_5Cl.2\text{-}3\,H_2O]_n$, which can be present in non-activated or in activated (depolymerized)

form, and aluminum chlorohydrate with the general formula $[Al_2(OH)_4Cl_2.1-6\ H_2O]_n$, preferably $[Al_2(OH)_4Cl_2.2-3\ H_2O]_n$, which can be present in non-activated or in activated (depolymerized) form.

The production of preferred active antiperspirant substances is disclosed, for example, in U.S. Pat. Nos. 3,887,692, 3,904,741, 4,359,456, GB 2048229 and GB 1347950.

Also preferred are aluminum sesquichlorohydrate, aluminum dichlorohydrate, aluminum chlorohydrex-propylene glycol (PG) or aluminum chlorohydrex-polyethylene glycol (PEG), aluminum glycol complexes, e.g. aluminum-propylene glycol complexes, aluminum sesquichlorohydrex-PG or aluminum sesquichlorohydrex-PEG, aluminum-PG dichlorohydrex or aluminum-PEG dichlorohydrex, aluminum hydroxide, also selected from potassium aluminum sulfate ($KAl(SO_4)_2.12\ H_2O$, alum), aluminum undecylenoyl collagen amino acid, sodium aluminum lactate+aluminum sulfate, sodium aluminum chlorohydroxylactate, aluminum bromohydrate, aluminum chloride, the complexes of zinc and sodium salts, the aluminum salts of lipoamino acids, aluminum sulfate, aluminum lactate, aluminum chlorohydroxyallantoinate, sodium-aluminum chlorohydroxylactate, zinc chloride, zinc sulfocarbolate and zinc sulfate.

Particularly preferred active antiperspirant substances according to the invention are selected from so-called "activated" aluminum salts, which are also referred to as active antiperspirant substances with enhanced activity. These active substances are known in the prior art and are also commercially available. Their production is disclosed, for example, in GB 2048229, U.S. Pat. Nos. 4,775,528 and 6,010,688. Activated aluminum salts are generally produced by heat treatment of a relatively dilute solution of the salt (e.g. about 10 wt. % salt), to increase its HPLC peak 4 to peak 3 area ratio. The activated salt can then be dried, in particular spray-dried, to form a powder. In addition to spray drying, roll drying is also suitable, for example.

Activated aluminum salts typically have an HPLC peak 4 to peak 3 area ratio of at least 0.4, preferably at least 0.7, particularly preferably at least 0.9, with at least 70% of the aluminum being assigned to these peaks.

Activated aluminum salts do not necessarily have to be used as a spray-dried powder. Other preferred active antiperspirant substances according to the invention are non-aqueous solutions or solubilizates of an activated antiperspirant aluminum salt, for example according to U.S. Pat. No. 6,010,688, which are stabilized against loss of activation against the rapid degradation of the HPLC peak 4:peak 3 area ratio of the salt by adding an effective quantity of a polyhydric alcohol having 3 to 6 carbon atoms and 3 to 6 hydroxyl groups, preferably propylene glycol, sorbitol and pentaerythritol. For example, compositions are preferred which contain, as percentages by weight (USP): 18-45 wt. % of an activated aluminum salt, 55-82 wt. % of at least one anhydrous polyhydric alcohol with 3 to 6 carbon atoms and 3 to 6 hydroxyl groups, preferably propylene glycol, butylene glycol, diethylene glycol, dipropylene glycol, glycerol, sorbitol and pentaerythritol, particularly preferably propylene glycol.

Particularly preferred are also complexes of activated antiperspirant aluminum salts with a polyhydric alcohol, which contain 20-50 wt. %, particularly preferably 20-42 wt. %, activated antiperspirant aluminum salt and 2-16 wt. % molecularly bound water, the remainder to 100 wt. % being at least one polyhydric alcohol with 3 to 6 carbon atoms and 3 to 6 hydroxyl groups. Propylene glycol, propylene glycol/sorbitol mixtures and propylene glycol/pentaerythritol mixtures are preferred alcohols of this type. Such complexes of an activated antiperspirant aluminum salt with a polyhydric alcohol, which are preferred according to the invention, are disclosed e.g. in U.S. Pat. Nos. 5,643,558 and 6,245,325.

Other preferred active antiperspirant substances are basic calcium-aluminum salts, as disclosed for example in U.S. Pat. No. 2,571,030. These salts are produced by reacting calcium carbonate with aluminum chlorhydroxide or aluminum chloride and aluminum powder or by adding calcium chloride dihydrate to aluminum chlorhydroxide.

Other preferred active antiperspirant substances are activated aluminum salts, as disclosed for example in U.S. Pat. Nos. 6,245,325 or 6,042,816, containing 5-78 wt. % (USP) of an activated antiperspirant aluminum salt, an amino acid or hydroxyalkanoic acid in such a quantity as to provide an (amino acid or hydroxyalkanoic acid) to aluminum weight ratio of 2:1-1:20 and preferably 1:1 to 1:10, and a water-soluble calcium salt in such a quantity as to provide a Ca:Al weight ratio of 1:1-1:28 and preferably 1:2-1:25.

Particularly preferred solid activated antiperspirant salt compositions, for example according to U.S. Pat. Nos. 6,245,325 or 6,042,816, contain 48-78 wt. % (USP), preferably 66-75 wt. %, of an activated aluminum salt and 1-16 wt. %, preferably 4-13 wt. %, of molecularly bound water (water of hydration), and also sufficient water-soluble calcium salt so that the Ca:Al weight ratio is 1:1-1:28, preferably 1:2-1:25, and sufficient amino acid so that the amino acid to (Al+Zr) weight ratio is 2:1-1:20, preferably 1:1-1:10.

Other particularly preferred solid antiperspirant activated salt compositions, for example according to U.S. Pat. Nos. 6,245,325 or 6,042,816, contain 48-78 wt. % (USP), preferably 66-75 wt. % of an activated aluminum salt and 1-16 wt. %, preferably 4-13 wt. %, of molecularly bound water (water of hydration), as well as sufficient water-soluble calcium salt so that the Ca:Al weight ratio is 1:1-1:28, preferably 1:2-1:25, and sufficient glycine so that the glycine to Al weight ratio is 2:1-1:20, preferably 1:1-1:10.

Other particularly preferred solid antiperspirant activated salt compositions, for example according to U.S. Pat. Nos. 6,245,325 or 6,042,816, contain 48-78 wt. % (USP), preferably 66-75 wt. % of an activated aluminum salt and 1-16 wt. %, preferably 4-13 wt. %, of molecularly bound water, as well as sufficient water-soluble calcium salt so that the Ca:Al weight ratio is 1:1-1:28, preferably 1:2-1:25, and sufficient hydroxyalkanoic acid so that the hydroxyalkanoic acid to Al weight ratio is 2:1-1:20, preferably 1:1-1:10.

Preferred water-soluble calcium salts for stabilizing the antiperspirant salts are selected from calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide and mixtures thereof.

Preferred amino acids for stabilizing the antiperspirant salts are selected from glycine, alanine, leucine, isoleucine, β-alanine, valine, cysteine, serine, tryptophan, phenylalanine, methionine, β-amino-n-butanoic acid and γ.amino-n-butanoic acid and the salts thereof, each in the d form, the l form and the dl form; glycine is particularly preferred.

Preferred hydroxyalkanoic acids for stabilizing the antiperspirant salts are selected from glycolic acid and lactic acid.

Other preferred active antiperspirant substances are activated aluminum salts, as disclosed for example in U.S. Pat. No. 6,902,723, containing 5-78 wt. % (USP) of an activated antiperspirant aluminum salt, an amino acid or hydroxyalkanoic acid in a sufficient quantity to provide an (amino acid or hydroxyalkanoic acid) to Al weight ratio of 2:1-1:20 and preferably 1:1 to 1:10, and a water-soluble strontium salt in a sufficient quantity to prepare an Sr:Al weight ratio of 1:1-1:28 and preferably 1:2-1:25.

Particularly preferred solid antiperspirant activated salt compositions, for example according to U.S. Pat. No. 6,902,723, contain 48-78 wt. % (USP), preferably 66-75 wt. %, of an activated aluminum salt and 1-16 wt. %, preferably 4-13 wt. %, of molecularly bound water, as well as sufficient water-soluble strontium salt so that the Sr:Al weight ratio is 1:1-1:28, preferably 1:2-1:25, and sufficient amino acid so that the amino acid to Al weight ratio is 2:1-1:20, preferably 1:1-1:10.

Other particularly preferred solid antiperspirant activated salt compositions, for example according to U.S. Pat. No. 6,902,723, contain 48-78 wt. % (USP), preferably 66-75 wt. %, of an activated aluminum salt and 1-16 wt. %, preferably 4-13 wt. %, of molecularly bound water, as well as sufficient water-soluble strontium salt so that the Sr:Al weight ratio is 1:1-1:28, preferably 1:2-1:25, and sufficient glycine so that the glycine to Al weight ratio is 2:1-1:20, preferably 1:1-1:10.

Other particularly preferred solid antiperspirant activated salt compositions, for example according to U.S. Pat. No. 6,902,723, contain 48-78 wt. % (USP), preferably 66-75 wt. % of an activated aluminum salt and 1-16 wt. %, preferably 4-13 wt. %, of molecularly bound water, as well as sufficient water-soluble strontium salt so that the Sr:Al weight ratio is 1:1-1:28, preferably 1:2-1:25, and sufficient hydroxyalkanoic acid so that the hydroxyalkanoic acid to Al weight ratio is 2:1-1:20, preferably 1:1-1:10.

Other preferred activated aluminum salts are those of the general formula $Al_2(OH)_{6-a}X_a$, wherein X is Cl, Br, I or $NO_3$ and "a" is a value from 0.3 to 5, preferably from 0.8 to 2.5 and particularly preferably 1 to 2, so that the molar ratio of Al:X is 0.9:1 to 2.1:1, as disclosed for example in U.S. Pat. No. 6,074,632. In these salts there is generally some associatively bound water of hydration, typically 1 to 6 moles of water per mole of salt. Particularly preferred is aluminum chlorohydrate (i.e. X is Cl in the aforementioned formula) and especially 5/6-basic aluminum chlorohydrate, wherein "a" is 1, so that the molar ratio of aluminum to chlorine is 1.9:1 to 2.1:1.

Other preferred active antiperspirant substances are disclosed in U.S. Pat. No. 6,663,854 and US 20040009133.

The active antiperspirant substances can be present both in solubilized and also in undissolved, suspended form.

Insofar as the active antiperspirant substances are present in suspension in a carrier that is immiscible with water, it is preferred for reasons of product stability that the active substance particles have a number-average particle size from 0.1-200 µm, preferably 1-50 µm, particularly preferably 3-20 µm and extraordinarily preferably 5-10 µm. Preferred active substance particles have a volume-average particle size from 0.2-220 µm, preferably 3-60 µm, particularly preferably 4-25 µm, further preferably 5-20 µm and extraordinarily preferably 10-15.5 µm.

Preferred aluminum salts have a molar metal to chloride ratio of from 1.9-2.1, or for sesquichlorohydrates from 1.5:1-1.8:1.

The active antiperspirant substances can be used as non-aqueous solutions or as glycolic solubilizates.

Particularly preferred compositions according to the invention are characterized in that the at least one active antiperspirant substance is contained in a quantity of 5-40 wt. %, preferably 10-35 wt. %, particularly preferably 15-28 wt. % and extraordinarily preferably 23-27 wt. %, based on the total weight of the active substance (USP) free from water of crystallization in the overall composition.

In a particularly preferred embodiment, the composition contains an astringent aluminum salt, in particular aluminum chlorohydrate, particularly preferably aluminum chlorohydrate with an active substance (USP) which is free from water of crystallization of 72-88 wt. %, based on the raw material as is. Preferred non-activated aluminum chlorohydrates are, for example, marketed in powder form as Micro Dry®, Micro Dry® Ultrafine or Micro Dry®-323 by Summit/Reheis, as Chlorhydrol® (powder) and in activated form as Reach® 101, Reach® 103, Reach® 501 by Reheis/Summit or AACH-7171 by Summit. Under the name Reach® 301, an aluminum sesquichlorohydrate, which is also particularly preferred, is offered by Reheis.

In a preferred embodiment according to the invention, the active antiperspirant substances and optionally other active substances that are insoluble in the carrier are suspended in at least one oil that is liquid under normal conditions. To improve the application properties, at least one preferably lipophilic thickener is also added to this suspension as a suspending aid. Other preferred compositions according to the invention are therefore characterized in that they contain at least one lipophilic thickener.

Preferred compositions according to the invention are characterized in that the at least one lipophilic thickener is selected from hydrophobically modified clay minerals, pyrogenic silicas, bentone gels, ethylene/propylene/styrene copolymers, butylene/ethylene/styrene copolymers, dextrin esters, silicone elastomers, waxes that are solid under normal conditions and/or glycerol triesters. Among these, hydrophobically modified clay minerals are particularly preferred. The compositions according to the invention contain, in a preferred embodiment, at least one suspending agent or thickener. Particularly suitable thickeners are hydrophobically modified clay minerals, such as montmorillonites, hectorites and bentonites, in particular disteardimonium hectorite and quaternium-18 hectorite. The commercial thickeners provide these hydrophobically modified clay minerals as powders or in the form of a pre-prepared gel in cyclomethicone and, if desired, a gel activator, such as e.g. propylene carbonate, ethanol or water. Other suitable thickeners are pyrogenic silicas, e.g. the commercial products from the Aerosil® range from Degussa.

Preferred hydrophobically modified clay minerals are selected from hydrophobically modified montmorillonites, hydrophobically modified hectorites and hydrophobically modified bentonites, particularly preferably from disteardimonium hectorite, stearalkonium hectorite, quaternium-18 hectorite and quaternium-18 bentonite. The commercial thickeners provide these hydrophobically modified clay minerals as powders or in the form of gels in an oil component, preferably in cyclomethicone and/or a non-silicone oil component, such as e.g. propylene carbonate. Gel formation takes place by adding small quantities of activators, such as in particular ethanol or propylene carbonate, but also water. Gels of this type are available, for example, with the trade name Bentone® or Thixogel.

Preferred compositions according to the invention are characterized in that they contain at least one hydrophobically modified clay mineral in a total quantity of 0.5-10 wt. %, preferably 1-7 wt. %, particularly preferably 2-6 wt. %, extraordinarily preferably 3-5 wt. %, based in each case on the total weight of the composition according to the invention.

These hydrophobically modified clay minerals generally require ethanol or propylene carbonate as activator in a quantity of 0.3-3 wt. %, preferably 0.5-2 wt. %, based in each case on the total weight of the composition according to the invention.

Other preferred lipophilic thickeners according to the invention are selected from pyrogenic silicas, e.g. the commercial products from the Aerosil® range from Evonik Degussa. Particularly preferred are hydrophobically modified pyrogenic silicas, particularly preferably silica silylates and silica dimethyl silylates.

Preferred compositions according to the invention are characterized in that they contain at least one pyrogenic silica, preferably at least one hydrophobically modified pyrogenic silica, in a total quantity of 0.5-10 wt. %, preferably 0.8-5 wt. %, particularly preferably 1-4 wt. %, extraordinarily preferably 1.5-2 wt. %, based in each case on the total weight of the composition according to the invention.

Other preferred compositions according to the invention are characterized in that they contain at least one hydrophilic pyrogenic silica, preferably in a total quantity of 0.1-10 wt. %, particularly preferably 0.3-5 wt. %, preferably 1-2 wt. %, extraordinarily preferably 0.7-1 wt. %, based in each case on the total weight of the composition according to the invention. Preferred hydrophilic pyrogenic silicas are available with the trade names Aerosil 200 (INCI: Silica) and Aerosil 300 (INCI: Silica).

Other preferred compositions according to the invention are characterized in that they contain at least one hydrophobically modified pyrogenic silica and at least one hydrophilic silica.

Other preferred lipophilic thickeners according to the invention are selected from ethylene/propylene/styrene copolymers and butylene/ethylene/styrene copolymers. The copolymers are particularly preferably used as a pre-thickened oil-based gel.

Preferred compositions according to the invention are characterized in that they contain at least one ethylene/propylene/styrene copolymer and/or butylene/ethylene/styrene copolymer in a total quantity of 0.05-3 wt. %, preferably 0.1-2 wt. %, particularly preferably 0.2-1.0 wt. %, extraordinarily preferably 0.3-0.5 wt. %, based in each case on the total weight of the composition according to the invention.

Other preferred lipophilic thickeners according to the invention are selected from silicone elastomers. Another preferred embodiment of the invention is characterized in that at least one silicone elastomer, which is obtainable by crosslinking an organopolysiloxane that contains at least 2 $C_2$-$C_{10}$ alkenyl groups with a terminal double bond in each molecule, with an organopolysiloxane having at least 2 silicone-bonded hydrogen atoms in each molecule, is contained.

Particularly preferred organopolysiloxanes according to the invention with at least 2 $C_2$-$C_{10}$ alkenyl groups with a terminal double bond in the molecule are selected from methyl vinyl siloxanes, methyl vinyl siloxane-dimethyl siloxane copolymers, dimethyl polysiloxanes with dimethyl vinyl siloxy end groups, dimethyl siloxane-methyl phenyl siloxane copolymers with dimethyl vinyl siloxy end groups, dimethyl siloxane-diphenyl siloxane-methyl vinyl siloxane copolymers with dimethyl vinyl siloxy end groups, dimethyl siloxane-methyl vinyl siloxane copolymers with trimethyl siloxy end groups, dimethyl siloxane-methyl phenyl siloxane-methyl vinyl siloxane copolymers with trimethyl siloxy end groups, methyl(3,3,3-trifluoropropyl)polysiloxanes with dimethyl vinyl siloxy end groups and dimethyl siloxane-methyl(3,3,3-trifluoropropyl) siloxane copolymers with dimethyl vinyl siloxy end groups.

Particularly preferred crosslinking organopolysiloxanes according to the invention with at least two silicone-bonded hydrogen atoms are selected from methyl hydrogen polysiloxanes with trimethyl siloxy end groups, dimethyl siloxane-methyl hydrogen siloxane copolymers with trimethyl siloxy end groups and cyclic dimethyl siloxane-methyl hydrogen siloxane copolymers.

Particularly preferred silicone elastomers according to the invention, which are already present as a raw material in a pre-swollen state in a silicone that is liquid at room temperature under normal conditions and represent a silicone-based gel, are commercially available, for example with the trade name SFE 168, a cyclomethicone (and) dimethicone/vinyl dimethicone cross polymer from GE Silicones, vinyl dimethicone cross polymers, contained in KSG-15 (cyclomethicone (and) dimethicone/vinyl dimethicone cross polymer, silicone elastomer content 4-10 wt. %), KSG-16 (dimethicone (and) dimethicone/vinyl dimethicone cross polymer, silicone elastomer content 20-30 wt. %), KSG-17 (cyclomethicone (and) dimethicone/vinyl dimethicone cross polymer), KSG-18 (phenyl trimethicone (and) dimethicone/phenyl vinyl dimethicone cross polymer, silicone elastomer content 10-20 wt. %); and KSG-20, available from Shin Etsu Silicones of America (Akron, Ohio), and from Grant Industries Inc. (Elmwood Park, N.J.) the products from the Gransil® range.

Another preferred embodiment of the invention is characterized in that the silicone elastomer can be obtained by crosslinking an organopolysiloxane, which contains at least 2 $C_2$-$C_{10}$ alkenyl groups with a terminal double bond in each molecule, with at least one alpha,omega-diene. Particularly preferred crosslinking alpha,omega-dienes according to the invention have the formula $CH_2$=$CH(CH_2)_x CH$=$CH_2$ with x=1–20. Particularly preferred alpha,omega-dienes are selected from 1,4-pentadiene, 1,5-hexadiene, 1,6-heptadiene, 1,7-octadiene, 1,8-nonadiene, 1,11-dodecadiene, 1,13-tetradecadiene and 1,19-eicosadiene.

Preferred compositions according to the invention are characterized in that they contain at least one silicone elastomer in a total quantity of 0.05-3 wt. %, preferably 0.1-2 wt. %, particularly preferably 0.15-0.5 wt. %, extraordinarily preferably 0.2-0.3 wt. %, based in each case on the total weight of the composition according to the invention.

Other preferred compositions according to the invention are characterized in that they contain at least one silicone rubber. Surprisingly, it has been found that, through the addition of a silicone rubber, the antiperspirant and deodorizing action of the compositions according to the invention can be further prolonged. Without wishing to be bound by this theory, it is assumed that the silicone rubber forms a film on the skin, as a result of which the active antiperspirant substance particles adhere better to the skin.

A particularly preferred silicone rubber according to the invention is selected from silicone polymers with the INCI name Dimethiconol. These dimethiconols are preferably used in a low-concentration solution in cyclomethicone or dimethicone with a kinematic viscosity from 0.65 cSt to no more than 10 cSt. Particularly preferred dimethiconols are available from Dow Corning with the trade names Dow Corning 1401, Dow Corning 1403 and Dow Corning 1501; these products contain 10 to 13 wt. % dimethiconol in cyclomethicone or dimethicone.

Preferred compositions according to the invention are characterized in that they contain at least one silicone rubber in a total quantity of 0.01-1.0 wt. %, preferably 0.05-0.2 wt. %, particularly preferably 0.1-0.15 wt. %, based in each case on the total weight of the composition according to the invention.

The compositions according to the invention contain at least one oil as carrier fluid.

Preferred antiperspirant compositions according to the invention contain 30-95 wt. %, preferably 40-93 wt. %, particularly preferably 50-90 wt. %, extraordinarily preferably 55-85 wt. %, based in each case on the overall composition, of at least one cosmetic oil that is liquid under normal conditions. Other preferred antiperspirant compositions according to the invention contain a total of 35-60 wt. %, preferably 40-55 wt. %, particularly preferably 45-50 wt. %, based in each case on the overall composition, of at least one cosmetic oil that is liquid under normal conditions. Also a total quantity of cosmetic oil that is liquid under normal conditions of 42, 43, 44, 46, 47, 48, 49, 51, 52, 53, 55, 58, 60, 63, 65, 68, 70, 73, 75, 78 or 80 wt. %, based in each case on the overall composition, can be particularly preferred according to the invention, with a total quantity of 45-55 wt. % being particularly preferred.

The cosmetic oils are differentiated into volatile and non-volatile oils. Non-volatile oils are understood to be those oils that have a vapor pressure of less than 2.66 Pa (0.02 mm Hg) at 20° C. and an atmospheric pressure of 1013 hPa. Volatile oils are understood to be those oils that have a vapor pressure of 2.66 Pa-40000 Pa (0.02 mm-300 mm Hg), preferably 12-12000 Pa (0.1-90 mm Hg), particularly preferably 13-8000 Pa, extraordinarily preferably 30-3000 Pa, further preferably 100-400 Pa, at 20° C. and an atmospheric pressure of 1013 hPa.

Preferred cosmetic oils according to the invention are selected from volatile silicone oils, which include e.g. dialkyl and alkylaryl siloxanes, such as for example cyclotetrasiloxane, cyclopentasiloxane, cyclohexasiloxane, dimethyl polysiloxane, low molecular-weight phenyl trimethicone and methyl phenyl polysiloxane, but also hexamethyl disiloxane, octamethyl trisiloxane and decamethyl tetrasiloxane. Particularly preferred are volatile silicone oils, which may be cyclic, such as e.g. octamethyl cyclotetrasiloxane, decamethyl cyclopentasiloxane and dodecamethyl cyclohexasiloxane and mixtures thereof, as are contained e.g. in the commercial products DC 244, 245, 344 and 345 from Dow Corning (vapor pressure at 20° C. approx. 13-15 Pa). Likewise particularly preferred are volatile linear silicone oils with 2-10 siloxane units, in particular hexamethyl disiloxane ($L_2$), octamethyl trisiloxane ($L_3$), decamethyl tetrasiloxane ($L_4$) and any mixtures of two or three of $L_2$, $L_3$ and/or $L_4$, preferably those mixtures as are contained e.g. in the commercial products DC2-1184, Dow Corning® 200 (0.65 cSt) and Dow Corning® 200 (1.5 cSt) from Dow Corning. Another preferred volatile silicone oil is a low molecular-weight phenyl trimethicone with a vapor pressure at 20° C. of about 2000 Pa, as is obtainable e.g. from GE Bayer Silicones/Momentive with the name Baysilone Fluid PD 5.

Volatile silicone oils are highly suitable carrier oils for preferred antiperspirant compositions according to the invention, since they provide them with a pleasant skin feel and low marking of clothes. Particularly preferred antiperspirant compositions according to the invention are therefore characterized by a content of at least one volatile silicone oil of 10-95 wt. %, preferably 30-80 wt. %, particularly preferably 40-70 wt. %, extraordinarily preferably 50-60 wt. %, based in each case on the overall composition.

As well as or instead of the at least one volatile silicone oil, at least one volatile non-silicone oil can also be contained. Preferred volatile non-silicone oils are selected from $C_8$-$C_{16}$ isoparaffins, in particular from isodecane, isoundecane, isododecane, isotridecane, isotetradecane, isopentadecane and isohexadecane, and mixtures thereof. $C_{10}$-$C_{13}$ isoparaffin mixtures are preferred, in particular those with a vapor pressure at 20° C. of about 10-400 Pa, preferably 13-300 Pa. This at least one volatile non-silicone oil is preferably contained in a total quantity of 10-95 wt. %, preferably 20-70 wt. %, particularly preferably 25-50 wt. %, extraordinarily preferably 30-40 wt. %, based in each case on the overall composition.

Owing to the dryer skin feel and the more rapid release of active substance, volatile silicone oils, isoparaffins, in particular selected from isodecane, isoundecane, isododecane, isotridecane, isotetradecane, isopentadecane, isohexadecane or isoeicosane, and mixtures of volatile silicone oils and isoparaffins, in particular selected from isododecane, isohexadecane and isoeicosane, are particularly preferred as carrier oil.

Preferred compositions according to the invention are characterized in that the at least one carrier oil b) which is liquid under normal conditions comprises at least one isoparaffin oil, in particular selected from isodecane, isoundecane, isododecane, isotridecane, isotetradecane, isopentadecane, isohexadecane and isoeicosane.

Other preferred compositions according to the invention are characterized in that the carrier oil b) which is liquid under normal conditions comprises a mixture of b)i) a volatile silicone oil, selected from cyclomethicone and linear polydimethylsiloxanes with 2-10 siloxane units, and b) ii) at least one isoparaffin oil, selected from isodecane, isoundecane, isododecane, isotridecane, isotetradecane, isopentadecane, isohexadecane and isoeicosane.

As well as the above-mentioned substances, generally referred to as "volatile" silicone oils, and as well as the aforementioned volatile non-silicone oils, particularly preferred antiperspirant compositions according to the invention can additionally contain at least one non-volatile cosmetic oil, selected from non-volatile silicone oils and non-volatile non-silicone oils. The at least one non-volatile oil compensates for the negative effect of the volatile oil on the residue behavior of preferred antiperspirant compositions according to the invention. As a result of the relatively rapid evaporation of the volatile oils, solid, insoluble components, in particular the active antiperspirant substances, can become visible on the skin as an unattractive residue. These residues can be successfully masked with a non-volatile oil. In addition, with a mixture of non-volatile and volatile oil, parameters such as skin feel, visibility of the residue and stability of the suspension can be finely regulated and better adapted to the requirements of the consumer.

Preferred non-volatile silicone oils are selected from higher molecular-weight linear dimethyl polysiloxanes, commercially available e.g. with the name Dow Corning® 190, Dow Corning® 200 Fluid with kinematic viscosities (25° C.) in the range of 5-100 cSt, preferably 6-50 cSt or 5-10 cSt, and Baysilon® 350 M (with a kinematic viscosity (25° C.) of about 350 cSt).

Likewise preferred silicone oils according to the invention are selected from silicones of the formula (Sil-1), wherein x is selected from integers from 1-20.

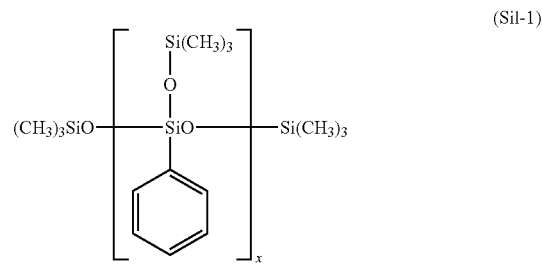

(Sil-1)

A preferred silicone oil of the formula (Sil-1) is available with the INCI name Phenyl Trimethicone in various grades, viscosities and volatilities. A non-volatile Phenyl Trimethicone is available, for example, from Dow Corning with the name Dow Corning 556.

Particularly preferred non-volatile non-silicone oils according to the invention are selected from the esters of the linear or branched, saturated or non-volatile non-silicone oils unsaturated fatty alcohols having 2-30 carbon atoms with linear or branched, saturated or unsaturated fatty acids having 2-30 carbon atoms, which may be hydroxylated. Among these, isopropyl palmitate, isopropyl stearate, isopropyl myristate, 2-ethylhexyl palmitate (Cegesoft® C 24) and 2-ethylhexyl stearate (Cetiol® 868) are extraordinarily preferred. Likewise preferred are hexyldecyl stearate (Eutanol® G16S), hexyldecyl laurate, isononyl isononanoate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyloctanoate, diisotridecyl acetate, n-hexyl laurate, n-decyl oleate, oleyl oleate, oleyl erucate, erucyl oleate and erucyl erucate.

Other preferred non-volatile non-silicone oils according to the invention are selected from the benzoic acid esters of linear or branched $C_{8-22}$ alkanols. Benzoic acid $C_{12}$-$C_{15}$ alkyl esters, e.g. obtainable as the commercial product Finsolv® TN, isostearyl benzoate, e.g. obtainable as the commercial product Finsolv® SB, ethylhexyl benzoate, e.g. obtainable as the commercial product Finsolv® EB, and octyldodecyl benzoate, e.g. obtainable as the commercial product Finsolv® BOD are particularly preferred, with benzoic acid $C_{12}$-$C_{15}$ alkyl esters being extraordinarily preferred.

Another preferred non-volatile non-silicone oil according to the invention is triethyl citrate.

Other particularly preferred non-volatile non-silicone oils according to the invention are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Other particularly preferred non-volatile non-silicone oils according to the invention are selected from the addition products of 1 to 5 propylene oxide units to mono- or polyhydric $C_{8-22}$ alkanols such as octanol, decanol, decanediol, lauryl alcohol, myristyl alcohol and stearyl alcohol, e.g. PPG-2 myristyl ether and PPG-3 myristyl ether (Witconol® APM).

Other particularly preferred non-volatile non-silicone oils according to the invention are selected from the addition products of at least 6 ethylene oxide and/or propylene oxide units to mono- or polyhydric $C_{3-22}$ alkanols such as glycerol, butanol, butanediol, myristyl alcohol and stearyl alcohol, which may be esterified if desired, e.g. PPG-14 butyl ether (Ucon Fluid® AP), PPG-9 butyl ether (Breox® B25), PPG-10 butanediol (Macol® 57), PPG-15 stearyl ether (Arlamol® E) and glycereth-7 diisononanoate.

Natural and synthetic hydrocarbons, such as for example paraffin oils, $C_{18}$-$C_{30}$ isoparaffins, in particular isoeicosane, polyisobutene or polydecene, which are available, for example, with the name Emery® 3004, 3006, 3010 or with the name Ethylflo® from Albemarle or Nexbase® 2004G from Nestle, and 1,3-di-(2-ethylhexyl)cyclohexane (available e.g. with the trade name Cetiol® S from Cognis), also belong to the preferred non-volatile non-silicone oils according to the invention.

Other preferred non-volatile non-silicone oils according to the invention are selected from branched, saturated or unsaturated fatty alcohols with 6-30 carbon atoms. These alcohols are often also referred to as Guerbet alcohols, as they are obtainable by the Guerbet reaction. Preferred alcohol oils are hexyl decanol (Eutanol® G 16), octyl dodecanol (Eutanol® G) and 2-ethylhexyl alcohol.

Other preferred non-volatile non-silicone oils are selected from mixtures of Guerbet alcohols and Guerbet alcohol esters, e.g. the commercial product Cetiol® PGL (hexyl decanol and hexyl decyl laurate).

Other preferred non-volatile non-silicone oils according to the invention are selected from the mono- and polyesters of lactic acid, citric acid, tartaric acid or adipic acid with a di-, tri- or tetrahydric alcohol having 2 to 9 carbon atoms. Particularly preferred esters of this type are selected from ethylene glycol monolactate, ethylene glycol monocitrate, ethylene glycol monotartrate, ethylene glycol monoadipate, ethylene glycol dilactate, ethylene glycol dicitrate, ethylene glycol ditartrate, ethylene glycol diadipate, 1,2-propylene glycol monolactate, 1,2-propylene glycol monocitrate, 1,2-propylene glycol monotartrate, 1,2-propylene glycol monoadipate, 1,2-propylene glycol dilactate, 1,2-propylene glycol dicitrate, 1,2-propylene glycol ditartrate, 1,2-propylene glycol diadipate, 1,3-propylene glycol monolactate, 1,3-propylene glycol monocitrate, 1,3-propylene glycol monotartrate, 1,3-propylene glycol monoadipate, 1,3-propylene glycol dilactate, 1,3-propylene glycol dicitrate, 1,3-propylene glycol ditartrate, 1,3-propylene glycol diadipate, 1,2-butylene glycol monolactate, 1,2-butylene glycol monocitrate, 1,2-butylene glycol monotartrate, 1,2-butylene glycol monoadipate, 1,2-butylene glycol dilactate, 1,2-butylene glycol dicitrate, 1,2-butylene glycol ditartrate, 1,2-butylene glycol diadipate, 1,3-butylene glycol monolactate, 1,3-butylene glycol monocitrate, 1,3-butylene glycol monotartrate, 1,3-butylene glycol monoadipate, 1,3-butylene glycol dilactate, 1,3-butylene glycol dicitrate, 1,3-butylene glycol ditartrate, 1,3-butylene glycol diadipate, 1,4-butylene glycol monolactate, 1,4-butylene glycol monocitrate, 1,4-butylene glycol monotartrate, 1,4-butylene glycol monoadipate, 1,4-butylene glycol dilactate, 1,4-butylene glycol dicitrate, 1,4-butylene glycol ditartrate, 1,4-butylene glycol diadipate, 1,2-pentanediol monolactate, 1,2-pentanediol monocitrate, 1,2-pentanediol monotartrate, 1,2-pentanediol monoadipate, 1,2-pentanediol dilactate, 1,2-pentanediol dicitrate, 1,2-pentanediol ditartrate, 1,2-pentanediol diadipate, 1,3-pentanediol monolactate, 1,3-pentanediol monocitrate, 1,3-pentanediol monotartrate, 1,3-pentanediol monoadipate, 1,3-pentanediol dilactate, 1,3-pentanediol dicitrate, 1,3-pentanediol ditartrate, 1,3-pentanediol diadipate, 1,4-pentanediol monolactate, 1,4-pentanediol monocitrate, 1,4-pentanediol monotartrate, 1,4-pentanediol monoadipate, 1,4-pentanediol dilactate, 1,4-pentanediol dicitrate, 1,4-pentanediol ditartrate, 1,4-pentanediol diadipate, 1,5-pentanediol monolactate, 1,5-pentanediol monocitrate, 1,5-pentanediol monotartrate, 1,5-pentanediol monoadipate, 1,5-pentanediol dilactate, 1,5-pentanediol dicitrate, 1,5-pentanediol ditartrate, 1,5-pentanediol diadipate, 1,2-hexanediol monolactate, 1,2-hexanediol monocitrate, 1,2-hexanediol monotartrate, 1,2-hexanediol monoadipate, 1,2-hexanediol dilactate, 1,2-hexanediol dicitrate, 1,2-hexanediol ditartrate, 1,2-hexanediol diadipate, 1,3-hexanediol monolactate, 1,3-hexanediol monocitrate, 1,3-hexanediol monotartrate, 1,3-hexanediol monoadipate, 1,3-hexanediol dilactate, 1,3-hexanediol dicitrate, 1,3-hexanediol ditartrate, 1,3-hexanediol diadipate, 1,4-hexanediol monolactate, 1,4-hexanediol monocitrate, 1,4- hexanediol monotartrate, 1,4-hexanediol monoadipate, 1,4-hexanediol dilactate, 1,4-hexanediol dicitrate, 1,4-hexanediol ditartrate, 1,4-hexanediol diadipate, 1,5-hexanediol monolactate, 1,5-hexanediol monocitrate, 1,5-hexanediol monotartrate, 1,5-hexanediol monoadipate, 1,5-hexanediol dilactate, 1,5-hexanediol dicitrate, 1,5-hexanediol ditartrate, 1,5-hexanediol diadipate, 1,6-hexanediol monolactate, 1,6-hexanediol monocitrate, 1,6-hexanediol monotartrate, 1,6-hexanediol monoadipate, 1,6-hexanediol dilactate, 1,6-hexanediol dicitrate, 1,6-hexanediol ditartrate, 1,6-hexanediol diadipate, 2-ethylhexane-1,2-diol monolactate, 2-ethylhexane-1,2-diol monocitrate, 2-ethylhexane-1,2-diol monotartrate, 2-ethylhexane-1,2-diol monoadipate, 2-ethylhexane-1,2-diol dilactate, 2-ethylhexane-1,2-diol dicitrate, 2-ethylhexane-1,2-diol ditartrate, 2-ethylhexane-1,2-diol diadipate, 2-ethylhexane-1,3-diol monolactate, 2-ethylhexane-1,3-diol monocitrate, 2-ethylhexane-1,3-diol monotartrate, 2-ethylhexane-1-diol monoadipate, 2-ethylhexane-1,3-diol dilactate, 2-ethylhexane-1,3-diol dicitrate, 2-ethylhexane-1,3-diol ditartrate, 2-ethylhexane-1,3-diol diadipate, 2-ethylhexane-1,4-diol monolactate, 2-ethylhexane-1,4-diol monocitrate, 2-ethylhexane-1,4-diol monotartrate, 2-ethylhexane-1,4-diol monoadipate, 2-ethylhexane-1,4-diol dilactate, 2-ethylhexane-1,4-diol dicitrate, 2-ethylhexane-1,4-diol ditartrate, 2-ethylhexane-1,4-diol diadipate, 2-ethylhexane-1,5-diol monolactate, 2-ethylhexane-1,5-diol monocitrate, 2-ethylhexane-1,5-diol monotartrate, 2-ethylhexane-1,5-diol monoadipate, 2-ethylhexane-1,5-diol dilactate, 2-ethylhexane-1,5-diol dicitrate, 2-ethylhexane-1,5-diol ditartrate, 2-ethylhexane-1,5-diol diadipate, 2-ethylhexane-1,6-diol monolactate, 2-ethylhexane-1,6-diol monocitrate, 2-ethylhexane-1,6-diol monotartrate, 2-ethylhexan-1,6-diol monoadipate, 2-ethylhexane-1,6-diol dilactate, 2-ethylhexane-1,6-diol dicitrate, 2-ethylhexane-1,6-diol ditartrate, 2-ethylhexan-1,6-diol diadipate, 1,2-heptanediol monolactate, 1,2-heptanediol monocitrate, 1,2-heptanediol monotartrate, 1,2-heptanediol monoadipate, 1,2-heptanediol dilactate, 1,2-heptanediol dicitrate, 1,2-heptanediol ditartrate, 1,2-heptanediol diadipate, 1,3-heptanediol monolactate, 1,3-heptanediol monocitrate, 1,3-heptanediol monotartrate, 1,3-heptanediol monoadipate, 1,3-heptanediol dilactate, 1,3-heptanediol dicitrate, 1,3-heptanediol ditartrate, 1,3-heptanediol diadipate, 1,4-heptanediol monolactate, 1,4-heptanediol monocitrate, 1,4-heptanediol monotartrate, 1,4-heptanediol monoadipate, 1,4-heptanediol dilactate, 1,4-heptanediol dicitrate, 1,4-heptanediol ditartrate, 1,4-heptanediol diadipate, 1,5-heptanediol monolactate, 1,5-heptanediol monocitrate, 1,5-heptanediol monotartrate, 1,5-heptanediol monoadipate, 1,5-heptanediol dilactate, 1,5-heptanediol dicitrate, 1,5-heptanediol ditartrate, 1,5-heptanediol diadipate, 1,6-heptanediol monolactate, 1,6-heptanediol monocitrate, 1,6-heptanediol monotartrate, 1,6-heptanediol monoadipate, 1,6-heptanediol dilactate, 1,6-heptanediol dicitrate, 1,6-heptanediol ditartrate, 1,6-heptanediol diadipate, 1,7-heptanediol monolactate, 1,7-heptanediol monocitrate, 1,7-heptanediol monotartrate, 1,7-heptanediol monoadipate, 1,7-heptanediol dilactate, 1,7-heptanediol dicitrate, 1,7-heptanediol ditartrate, 1,7-heptanediol diadipate, 1,2-octanediol monolactate, 1,2-octanediol monocitrate, 1,2-octanediol monotartrate, 1,2-octanediol monoadipate, 1,2-octanediol dilactate, 1,2-octanediol dicitrate, 1,2-octanediol ditartrate, 1,2-octanediol diadipate, 1,3-octanediol monolactate, 1,3-octanediol monocitrate, 1,3-octanediol monotartrate, 1,3-octanediol monoadipate, 1,3-octanediol dilactate, 1,3-octanediol dicitrate, 1,3-octanediol ditartrate, 1,3-octanediol diadipate, 1,4-octanediol monolactate, 1,4-octanediol monocitrate, 1,4-octanediol monotartrate, 1,4-octanediol monoadipate, 1,4-octanediol dilactate, 1,4-octanediol dicitrate, 1,4-octanediol ditartrate, 1,4-octanediol diadipate, 1,5-octanediol monolactate, 1,5-octanediol monocitrate, 1,5-octanediol monotartrate, 1,5-octanediol monoadipate, 1,5-octanediol dilactate, 1,5-octanediol dicitrate, 1,5-octanediol ditartrate, 1,5-octanediol diadipate, 1,6-octanediol monolactate, 1,6-octanediol monocitrate, 1,6-octanediol monotartrate, 1,6-octanediol monoadipate, 1,6-octanediol dilactate, 1,6-octanediol dicitrate, 1,6-octanediol ditartrate, 1,6-octanediol diadipate, 1,7-octanediol monolactate, 1,7-octanediol monocitrate, 1,7-octanediol monotartrate, 1,7-octanediol monoadipate, 1,7-octanediol dilactate, 1,7-octanediol dicitrate, 1,7-octanediol ditartrate, 1,7-octanediol diadipate, 1,8-octanediol monolactate, 1,8-octanediol monocitrate, 1,8-octanediol monotartrate, 1,8-octanediol monoadipate, 1,8-octanediol dilactate, 1,8-octanediol dicitrate, 1,8-octanediol ditartrate, 1,8-octanediol diadipate, 2-methyl-1,3-propanediol monolactate, 2-methyl-1,3-propanediol monocitrate, 2-methyl-1,3-propanediol monotartrate, 2-methyl-1,3-propanediol monoadipate, 2-methyl-1,3-propanediol dilactate, 2-methyl-1,3-propanediol dicitrate, 2-methyl-1,3-propanediol ditartrate, 2-methyl-1,3-propanediol diadipate, dipropylene glycol monolactate, dipropylene glycol monotartrate, dipropylene glycol monocitrate, dipropylene glycol monoadipate, dipropylene glycol dilactate, dipropylene glycol ditartrate, dipropylene glycol dicitrate, dipropylene glycol diadipate, glycerol monolactate, glycerol monotartrate, glycerol monocitrate, glycerol monoadipate, glycerol dilactate, glycerol ditartrate, glycerol dicitrate, glycerol diadipate, glycerol trilactate, glycerol tritartrate, glycerol tricitrate, glycerol triadipate, diglycerol monolactate, diglycerol monotartrate, diglycerol monocitrate, diglycerol monoadipate, diglycerol dilactate, diglycerol ditartrate, diglycerol dicitrate, diglycerol diadipate, diglycerol trilactate, diglycerol tritartrate, diglycerol tricitrate, diglycerol triadipate, tripropylene glycol monolactate, tripropylene glycol monotartrate, tripropylene glycol monocitrate, tripropylene glycol monoadipate, tripropylene glycol dilactate, tripropylene glycol ditartrate, tripropylene glycol dicitrate, tripropylene glycol diadipate, tripropylene glycol trilactate, tripropylene glycol tritartrate, tripropylene glycol tricitrate, tripropylene glycol triadipate, triglycerol monolactate, triglycerol monotartrate, triglycerol monocitrate, triglycerol monoadipate, triglycerol dilactate, triglycerol ditartrate, triglycerol dicitrate, triglycerol diadipate, triglycerol trilactate, triglycerol tritartrate, triglycerol tricitrate, triglycerol triadipate, 1,2,6-hexanetriol monolactate, 1,2,6-hexanetriol monotartrate, 1,2,6-hexanetriol monocitrate, 1,2,6-hexanetriol monoadipate, 1,2,6-hexanetriol dilactate, 1,2,6-hexanetriol ditartrate, 1,2,6-hexanetriol dicitrate, 1,2,6-hexanetriol diadipate, 1,2,6-hexanetriol trilactate, 1,2,6-hexanetriol tritartrate, 1,2,6-hexanetriol tricitrate, 1,2,6-hexanetriol triadipate, trimethylolpropane monolactate, trimethylolpropane monotartrate, trimethylolpropane monocitrate, trimethylolpropane monoadipate, trimethylolpropane dilactate, trimethylolpropane ditartrate, trimethylolpropane dicitrate, trimethylolpropane diadipate, trimethylolpropane trilactate, trimethylolpropane tritartrate, trimethylolpropane tricitrate, trimethylolpropane triadipate, trimethylolethane monolactate, trimethylolethane monotartrate, trimethylolethane monocitrate, trimethylolethane monoadipate, trimethylolethane dilactate, trimethylolethane ditartrate, trimethylolethane dicitrate, trimethylolethane diadipate, trimethylolethane trilactate, trimethylolethane tritartrate, trimethylolethane tricitrate and trimethylolethane triadipate, and mixtures thereof.

Other preferred non-volatile non-silicone oils according to the invention are selected from the triglycerides of linear or branched, saturated or unsaturated, optionally hydroxylated $C_{8-30}$ fatty acids. The use of natural oils can be particularly suitable, e.g. soybean oil, cottonseed oil, sunflower oil, palm oil, palm kernel oil, linseed oil, almond oil, castor oil, maize oil, rapeseed oil, olive oil, sesame oil, thistle oil, wheat germ oil, peach kernel oil and the liquid fractions of coconut oil and the like. However, synthetic triglyceride oils are also suitable, in particular capric/caprylic triglycerides, e.g. the commercial products Myritol® 318, Myritol® 331 (Cognis) or Miglyol® 812 (Hüls) with unbranched fatty acid residues and glyceryl triisostearin and the commercial products Estol® GTEH 3609 (Uniqema) or Myritol® GTEH (Cognis) with branched fatty acid residues.

Other particularly preferred non-volatile non-silicone oils according to the invention are selected from the symmetrical, asymmetrical or cyclic esters of carbonic acid with fatty alcohols, e.g. glycerol carbonate, dicaprylyl carbonate (Cetiol® CC), di-n-octyl carbonate, di-n-dodecyl carbonate, di(2-ethylhexyl) carbonate or the esters according to the teaching of DE 19756454 A. Other oils that may be preferred according to the invention are selected from the esters of dimers of unsaturated $C_{12}$-$C_{22}$ fatty acids (dimer fatty acids) with monohydric linear, branched or cyclic $C_2$-$C_{18}$ alkanols or with polyhydric linear or branched $C_2$-$C_6$ alkanols.

It can be extraordinarily preferred according to the invention to use mixtures of the aforementioned oils in order to achieve optimum fine adjustment of the product properties, in particular the stick properties, such as stick hardness, residue behavior, rub-off properties or active substance release.

Other preferred compositions according to the invention are characterized in that at least one non-volatile non-silicone oil is contained in a total quantity of 10-95 wt. %, preferably 15-75 wt. %, particularly preferably 18-50 wt. %, extraordinarily preferably 20-35 wt. %, based in each case on the overall composition.

According to another, also preferred embodiment, the water-free antiperspirant compositions according to the invention contain a small proportion of no more than 2 wt. %, preferably no more than 1 wt. %, of cyclomethicone or are even free from cyclomethicone. As a substitute for cyclomethicone, the $C_8$-$C_{16}$ isoparaffins, in particular selected from isononane, isodecane, isoundecane, isododecane, isotridecane, isotetradecane, isopentadecane and isohexadecane, and mixtures thereof, are particularly preferred. $C_{10}$-$C_{13}$ isoparaffin mixtures are preferred, in particular those with a vapor pressure at 20° C. of about 8-400 Pa, preferably 13-300 Pa.

In addition to the at least one aforementioned $C_8$-$C_{16}$ isoparaffin, other preferred antiperspirant compositions according to the invention contain, as well as 0 to no more than 2 wt. %, preferably no more than 1 wt. %, of cyclomethicone, at least one non-volatile cosmetic oil, selected from non-volatile silicone oils and non-volatile non-silicone oils. The at least one non-volatile oil compensates for the negative effect of the volatile isoparaffins on the residue behavior of preferred antiperspirant compositions according to the invention. As a result of the relatively rapid evaporation of the volatile oils, solid, insoluble components, in particular the active antiperspirant substances, can become visible on the skin as an unattractive residue. These residues can be successfully masked with a non-volatile oil. In addition, with a mixture of non-volatile and volatile oil, parameters such as skin feel, visibility of the residue and stability of the suspension can be finely regulated and better adapted to the requirements of the consumer. Particularly preferred non-volatile oils for this purpose are, in particular, the ester oils 2-ethylhexyl palmitate (e.g. Cegesoft® C 24), hexyldecyl laurate, 2-ethylhexyl stearate, isopropyl myristate, isopropyl palmitate and 2-ethylhexyl laurate, the benzoic acid esters of linear or branched $C_{8-22}$ alkanols, in particular the commercial product Finsolv® TN ($C_{12}$-$C_{15}$ alkyl benzoate), $C_{12}$-$C_{15}$ alkyl lactate and di-$C_{12}$-$C_{13}$ alkyl malate are suitable. It can also be particularly preferred to formulate water-free antiperspirant compositions according to the invention without cyclomethicone and without volatile linear silicone oils. For this purpose too, the esters oils 2-ethylhexyl palmitate (e.g. Cegesoft® C 24), hexyldecyl laurate, 2-ethylhexyl stearate, isopropyl myristate, isopropyl palmitate and 2-ethylhexyl laurate, the benzoic acid esters of linear or branched $C_{8-22}$ alkanols, in particular the commercial product Finsolv® TN ($C_{12}$-$C_{15}$ alkyl benzoate), $C_{12}$-$C_{15}$ alkyl lactate and di-$C_{12}$-$C_{13}$ alkyl malate are particularly preferably suitable.

Particularly preferred oil mixtures according to the invention with 0 to no more than 2 wt. %, preferably 0 to no more than 1 wt. %, of cyclomethicone are 2-ethylhexyl palmitate/isodecane/isoundecane/isododecane/isotridecane, hexyldecyl laurate/isodecane/isoundecane/isododecane/isotridecane, 2-ethylhexyl stearate/isodecane/isoundecane/isododecane/isotridecane, isopropyl myristate/isodecane/isoundecane/isododecane/isotridecane, isopropyl palmitate/isononane/isodecane/isoundecane/isododecane/
isotridecane, 2-ethylhexyl laurate/isodecane/isoundecane/isododecane/isotridecane, $C_{12}$-$C_{15}$ alkyl lactate/isodecane/isoundecane/isododecane/isotridecane, $C_{12}$-$C_{15}$ alkyl benzoate/isodecane/isoundecane/isododecane/isotridecane and di-$C_{12}$-$C_{13}$ alkyl malate/isodecane/isoundecane/isododecane/isotridecane.

In preferred oil mixtures with 0 to no more than 2 wt. %, preferably 0 to no more than 1 wt. %, of cyclomethicone, the two types of oil (esters/$C_8$-$C_{16}$ isoparaffin) are contained in approximately equal proportions by weight, i.e. in weight ratios of esters/$C_8$-$C_{16}$ isoparaffin of 0.9 to 1.2, preferably 1 to 1.1.

In other preferred embodiments of the invention, there is an excess of $C_8$-$C_{16}$ isoparaffin compared with the ester(s). In these cases, the weight ratio of esters/$C_{8-16}$ isoparaffin is preferably 0.1 to 0.8, particularly preferably 0.3 to 0.6, and extraordinarily preferably 0.4 to 0.5.

In other preferred oil mixtures with 0 to no more than 2 wt. %, preferably 0 to no more than 1 wt. %, of cyclomethicone, the two types of oil, isopropyl myristate/$C_8$-$C_{16}$ isoparaffin, are contained in approximately equal proportions by weight, i.e. in weight ratios of ester/$C_8$-$C_{16}$ isoparaffin of 0.9 to 1.2, preferably 1 to 1.1. Other preferred weight ratios of isopropyl myristate/$C_{8-16}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, isopropyl palmitate/$C_8$-$C_{16}$ isoparaffin, are contained in approximately equal proportions by weight, i.e. in weight ratios of ester/$C_8$-$C_{16}$ isoparaffin of 0.9 to 1.2, preferably 1 to 1.1. Other preferred weight ratios of isopropyl palmitate/$C_{8-16}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, 2-ethylhexyl palmitate/$C_8$-$C_{16}$ isoparaffin, are contained in approximately equal proportions by weight, i.e. in weight ratios of ester/$C_8$-$C_{16}$ isoparaffin of 0.9 to 1.2, preferably 1 to 1.1. Other preferred weight ratios of 2-ethylhexyl palmitate/$C_{8-16}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, $C_{12}$-$C_{15}$ alkyl benzoate/$C_8$-$C_{16}$ isoparaffin, are contained in approximately equal proportions by weight, i.e. in weight ratios of esters/$C_8$-$C_{16}$ isoparaffin of 0.9 to 1.2, preferably 1 to 1.1. Other preferred weight ratios of $C_{12}$-$C_{15}$ alkyl benzoate/$C_{8-16}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, esters/$C_{10}$-$C_{13}$ isoparaffin, are contained in approximately equal proportions by weight, i.e. in weight ratios of esters/$C_{10}$-$C_{13}$ isoparaffin of 0.9 to 1.2, preferably 1 to 1.1. Other preferred weight ratios of esters/$C_{10-13}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, isopropyl myristate/$C_{10}$-$C_{13}$ isoparaffin, are contained in approximately equal proportions by weight, i.e. in weight ratios of ester/$C_{10}$-$C_{13}$ isoparaffin of 0.9 to 1.2, preferably 1 to 1.1. Other preferred weight ratios of isopropyl myristate/$C_{10-13}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, isopropyl palmitate/$C_{10}$-$C_{13}$ isoparaffin, are contained in approximately equal proportions by weight, i.e. in weight ratios of ester/$C_{10}$-$C_{13}$ isoparaffin of 0.9 to 1.2, preferably 1 to 1.1. Other preferred weight ratios of isopropyl palmitate/$C_{10-13}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, 2-ethylhexyl palmitate/$C_{10}$-$C_{13}$ isoparaffin, are contained in approximately equal proportions by weight, i.e. in weight ratios of ester/$C_{10}$-$C_{13}$ isoparaffin of 0.9 to 1.2, preferably 1 to 1.1. Other preferred weight ratios of 2-ethylhexyl palmitate/$C_{10-13}$ isoparaffin are in the range from 0.1 to 0.8, particularly preferably 0.3 to 0.6, extraordinarily preferably 0.4 to 0.5.

In other preferred oil mixtures with 0 to no more than 2 wt. %, preferably 0 to no more than 1 wt. %, of cyclomethicone, the two types of oil, $C_{12}$-$C_{15}$ alkyl benzoate/$C_{10}$-$C_{13}$ isoparaffin, are contained in approximately equal proportions by weight, i.e. in weight ratios of esters/$C_{10}$-$C_{13}$ isoparaffin of 0.9 to 1.2, preferably 1 to 1.1. Other preferred weight ratios of $C_{12}$-$C_{15}$ alkyl benzoate/$C_{10-13}$ isoparaffin are in the range from 0.1 to 0.8, particularly preferably 0.3 to 0.6, extraordinarily preferably 0.4 to 0.5.

Particularly preferred compositions according to the invention are characterized in that the carrier oil b) which is liquid under normal conditions comprises a mixture b)i)+b)ii)+b)iii) of b)i) an ester oil selected from 2-ethylhexyl palmitate, isopropyl myristate and isopropyl palmitate, and b)ii) at least one isoparaffin oil, selected from isodecane, isoundecane, isododecane, isotridecane, isotetradecane, isopentadecane, isohexadecane and isoeicosane, and b)iii) O—no more than 1 wt. % cyclomethicone.

Other particularly preferred compositions according to the invention are characterized in that the carrier oil b) which is liquid under normal conditions consists of a mixture b)i)+b)ii)+b)iii) of b)i) an ester oil, selected from 2-ethylhexyl palmitate, isopropyl myristate and isopropyl palmitate, and b)ii) at least one isoparaffin oil, selected from isodecane, isoundecane, isododecane, isotridecane, isotetradecane, isopentadecane, isohexadecane and isoeicosane, and b)iii) 0 to no more than 1 wt. % cyclomethicone.

Other preferred compositions according to the invention are characterized in that the carrier oil which is liquid under normal conditions is selected from a mixture of triethyl citrate and at least one other cosmetic oil which is liquid under normal conditions as carrier, wherein the proportion by weight of triethyl citrate in the total quantity of oils, based on the overall composition, is 13-50 wt. % and 0 to less than 1 wt. % of cyclomethicone, based on the weight of the composition, is contained. The proportion by weight of triethyl citrate in the total oil content is preferably 12-40 wt. %, particularly preferably 16-35 wt. %, extraordinarily preferably 20-30 wt. %.

Particularly preferred oil mixtures according to the invention are triethyl citrate/2-ethylhexyl palmitate/isodecane/isoundecane/isododecane/isotridecane, triethyl citrate/hexyldecyl laurate/isodecane/isoundecane/isododecane/isotridecane, triethyl citrate/2-ethylhexyl stearate/isodecane/isoundecane/isododecane/isotridecane, triethyl citrate/isopropyl myristate/isodecane/isoundecane/isododecane/isotridecane, triethyl citrate/isopropyl palmitate/isononane/isodecane/isoundecane/isododecane/isotridecane, triethyl citrate/2-ethylhexyl laurate/isodecane/isoundecane/isododecane/isotridecane, triethyl citrate/$C_{12}$-$C_{15}$ alkyl lactate/isodecane/isoundecane/isododecane/isotridecane, triethyl citrate/$C_{12}$-$C_{15}$ alkyl benzoate/isodecane/isoundecane/isododecane/isotridecane and triethyl citrate/di-$C_{12}$-$C_{13}$ alkyl malate/isodecane/isoundecane/isododecane/isotridecane.

In preferred oil mixtures, all three types of oil (triethyl citrate/ester/$C_8$-$C_{16}$ isoparaffin) are contained in equal proportions by weight. Other preferred weight ratios of triethyl citrate/ester/$C_{8-16}$ isoparaffin are (1-1.3):(0.6-1):(1-3). Other preferred weight ratios of triethyl citrate/ester/$C_8$-$C_{16}$ isoparaffin are (1-1.3):1:(1-1.5). Other preferred weight ratios of triethyl citrate/esters/$C_8$-$C_{16}$ isoparaffin are (1-1.3):(0.6-0.9):(2.5-3), in particular 1:0.8:3.

In preferred oil mixtures, all three types of oil (triethyl citrate/isopropyl myristate/$C_8$-$C_{16}$ isoparaffin) are contained in equal proportions by weight. Other preferred weight ratios of triethyl citrate/isopropyl myristate/$C_{8-16}$ isoparaffin are (1-1.3):(0.6-1):(1-3). Other preferred weight ratios of triethyl citrate/isopropyl myristate/$C_8$-$C_{16}$ isoparaffin are (1-1.3):1:(1-1.5). Other preferred weight ratios of triethyl citrate/isopropyl myristate/$C_8$-$C_{16}$ isoparaffin are (1-1.3):(0.6-0.9):(2.5-3), in particular 1:0.8:3.

In preferred oil mixtures, all three types of oil (triethyl citrate/isopropyl palmitate/$C_8$-$C_{16}$ isoparaffin) are contained in equal proportions by weight. Other preferred weight ratios of triethyl citrate/isopropyl palmitate/$C_{8-16}$ isoparaffin are (1-1.3):(0.6-1):(1-3). Other preferred weight ratios of triethyl citrate/isopropyl palmitate/$C_8$-$C_{16}$ isoparaffin are (1-1.3):1:(1-1.5). Other preferred weight ratios of triethyl citrate/isopropyl palmitate/$C_8$-$C_{16}$ isoparaffin are (1-1.3):(0.6-0.9):(2.5-3), in particular 1:0.8:3.

In preferred oil mixtures, all three types of oil (triethyl citrate/$C_{12}$-$C_{15}$ alkyl benzoate/$C_8$-$C_{16}$ isoparaffin) are contained in equal proportions by weight. Other preferred weight ratios of triethyl citrate/$C_{12}$-$C_{15}$ alkyl benzoate/$C_{8-16}$ isoparaffin are (1-1.3):(0.6-1):(1-3). Other preferred weight ratios of triethyl citrate/$C_{12}$-$C_{15}$ alkyl benzoate/$C_8$-$C_{16}$ isoparaffin are (1-1.3):1:(1-1.5). Other preferred weight ratios of triethyl citrate/$C_{12}$-$C_{15}$ alkyl benzoate/$C_8$-$C_{16}$ isoparaffin are (1-1.3):(0.6-0.9):(2.5-3), in particular 1:0.8:3.

In other preferred oil mixtures, all three types of oil (triethyl citrate/ester/$C_{10}$-$C_{13}$ isoparaffin) are contained in equal proportions by weight. Other preferred weight ratios of triethyl citrate/ester/$C_{10-13}$ isoparaffin are (1-1.3):(0.6-1):(1-3). Other preferred weight ratios of triethyl citrate/ester/$C_{10}$-$C_{13}$ isoparaffin are (1-1.3): 1:(1-1.5). Other preferred weight ratios of triethyl citrate/ester/$C_{10}$-$C_{13}$ isoparaffin are (1-1.3):(0.6-0.9):(2.5-3), in particular 1:0.8:3.

In preferred oil mixtures, all three types of oil (triethyl citrate/isopropyl myristate/$C_{10}$-$C_{13}$ isoparaffin) are contained in equal proportions by weight. Other preferred weight ratios of triethyl citrate/isopropyl myristate/$C_{10}$-$C_{13}$ isoparaffin are (1-1.3):(0.6-1):(1-3). Other preferred weight ratios of triethyl citrate/isopropyl myristate/$C_{10}$-$C_{13}$ isoparaffin are (1-1.3): 1:(1-1.5). Other preferred weight ratios of triethyl citrate/isopropyl myristate/$C_{10}$-$C_{13}$ isoparaffin are (1-1.3):(0.6-0.9):(2.5-3), in particular 1:0.8:3.

In preferred oil mixtures, all three types of oil (triethyl citrate/isopropyl palmitate/$C_{10}$-$C_{13}$ isoparaffin) are contained in equal proportions by weight. Other preferred weight ratios of triethyl citrate/isopropyl palmitate/$C_{10-13}$ isoparaffin are (1-1.3):(0.6-1):(1-3). Other preferred weight ratios of triethyl citrate/isopropyl palmitate/$C_{10}$-$C_{13}$ isoparaffin are (1-1.3):1:(1-1.5). Other preferred weight ratios of triethyl citrate/isopropyl palmitate/$C_{10}$-$C_{13}$ isoparaffin are (1-1.3):(0.6-0.9):(2.5-3), in particular 1:0.8:3.

In other preferred oil mixtures, all three types of oil (triethyl citrate/$C_{12}$-$C_{15}$ alkyl benzoate/$C_{10}$-$C_{13}$ isoparaffin) are contained in equal proportions by weight. Other preferred weight ratios of triethyl citrate/$C_{12}$-$C_{15}$ alkyl benzoate/$C_{10-13}$ isoparaffin are (1-1.3):(0.6-1):(1-3). Other preferred weight ratios of triethyl citrate/$C_{12}$-$C_{15}$ alkyl benzoate/$C_{10}$-$C_{13}$ isoparaffin are (1-1.3):1:(1-1.5). Other preferred weight ratios of triethyl citrate/$C_{12}$-$C_{15}$ alkyl benzoate/$C_{10}$-$C_{13}$ isoparaffin are (1-1.3):(0.6-0.9):(2.5-3), in particular 1:0.8:3.

It may be extraordinarily preferred according to the invention to use mixtures of the aforementioned oils in order to achieve optimum fine adjustment of the product properties, in particular of the residue behavior, the skin feel or the active substance release.

Other preferred compositions according to the invention, in particular those in the form of sticks and soft solids, are characterized in that they contain at least one fatty component which is solid under normal conditions with a melting point of more than 50-120° C. Preferred fatty components with a melting point of >50-120° C. are selected from waxes. In general, waxes are of a solid to brittle-hard consistency, coarse to finely crystalline, translucent to opaque, but non-glassy, and melt at above 50° C. without decomposing. They are already of low viscosity just slightly above the melting point and display a highly temperature-dependent consistency and solubility.

Preferred according to the invention are, for example, natural plant waxes, e.g. candelilla wax, carnauba wax, Japan wax, sugarcane wax, ouricuri wax, cork wax, sunflower wax, fruit waxes such as orange waxes, lemon waxes, grapefruit wax, and animal waxes, e.g. beeswax, shellac wax and cetaceum. Within the meaning of the invention it can be particularly preferred to use hydrogenated or hardened waxes. As wax component, chemically modified waxes, in particular the hard waxes, such as e.g. montan ester waxes, hydrogenated jojoba waxes and Sasol waxes, can also be used. The synthetic waxes, which are also preferred according to the invention, include for example polyalkylene waxes, in particular polyethylene waxes, and polyethylene glycol waxes, $C_{20}$-$C_{40}$ dialkyl esters of dimer acids, $C_{30-50}$ alkyl beeswax and alkyl and alkylaryl esters of dimer fatty acids.

A particularly preferred wax component is selected from at least one ester of a saturated, monohydric $C_{16}$-$C_{60}$ alcohol and a saturated $C_8$-$C_{36}$ monocarboxylic acid. According to the invention, these also include lactides, the cyclic double esters of α-hydroxycarboxylic acids with the appropriate chain length. Esters of fatty acids and long-chain alcohols have proved particularly advantageous for the preferred compositions according to the invention, because they provide excellent sensory properties and—for the sticks—high stability. The esters are composed of saturated, branched or unbranched monocarboxylic acids and saturated, branched or unbranched monohydric alcohols. Esters of aromatic carboxylic acids or hydroxycarboxylic acids (e.g. 12-hydroxystearic acid) and saturated, branched or unbranched alcohols can also be used according to the invention, provided that the wax component has a melting point >50° C. It is particularly preferred to select the wax components from the group of the esters of saturated, branched or unbranched alkane carboxylic acids with a chain length of 12 to 24 C atoms and the saturated, branched or unbranched alcohols with a chain length of 16 to 50 C atoms, which have a melting point >50° C.

In particular, $C_{16-36}$ alkyl stearates and $C_{18-38}$ alkyl hydroxystearoyl stearates, $C_{20-40}$ alkyl erucates and cetearyl behenate may be preferred as wax component. The wax or the wax components have a melting point >50° C., preferably >60° C.

A particularly preferred embodiment of the invention contains as wax component a $C_{20}$-$C_{40}$ alkyl stearate. This ester is known by the name Kester Wax® K82H or Kester Wax® K80H and is marketed by Koster Keunen Inc. It is the synthetic copy of the monoester fraction of beeswax and is distinguished by its hardness, its oil gelling properties and its broad compatibility with lipid components. Kester Wax offers the advantage that it also has excellent oil gelling properties even at low concentrations, so making the stick or soft solid mass not too heavy and allowing a velvety application. Another particularly preferred embodiment of the invention contains cetearyl behenate, i.e. mixtures of cetyl behenate and stearyl behenate, as the wax component. This ester is known by the name Kester Wax® K62 and is marketed by Koster Keunen Inc.

Other preferred wax components with a melting point >50° C. are the triglycerides of saturated and optionally hydroxylated $C_{12-30}$ fatty acids, such as hydrogenated triglyceride fats (hydrogenated palm oil, hydrogenated coconut oil, hydrogenated castor oil), glyceryl tribehenate (tribehenin) or glyceryl tri(12-hydroxystearate), and also synthetic full esters of fatty acids and glycols or polyols with 2-6 carbon atoms, provided that they have a melting point greater than 50° C., for example preferably $C_{18}$-$C_{36}$ acid triglyceride (Syncrowax® HGL-C).

According to the invention, hydrogenated castor oil, obtainable e.g. as the commercial product Cutina® HR, is particularly preferred as the wax component.

Other preferred wax components with a melting point >50° C. are the saturated linear $C_{14}$-$C_{36}$ carboxylic acids, in particular myristic acid, palmitic acid, stearic acid and behenic acid and mixtures of these compounds, e.g. Syncrowax® AW 1C ($C_{18}$-$C_{36}$ fatty acids) or Cutina® FS 45 (palmitic and stearic acid).

Preferred compositions according to the invention are characterized in that the wax component as a constituent of the carrier according to the invention is selected from esters of a saturated, monohydric $C_{16}$-$C_{60}$ alkanol and a saturated $C_8$-$C_{36}$ monocarboxylic acid, in particular cetyl behenate, stearyl behenate and $C_{20}$-$C_{40}$ alkyl stearate, glycerol triesters of saturated linear $C_{12}$-$C_{30}$ carboxylic acids, which can be hydroxylated, candelilla wax, carnauba wax, beeswax, saturated linear $C_{14}$-$C_{36}$ carboxylic acids and mixtures of the aforementioned substances. Particularly preferred mixtures of wax components are selected from mixtures of cetyl behenate, stearyl behenate, hydrogenated castor oil, palmitic acid and stearic acid. Other particularly preferred mixtures of wax components are selected from mixtures of $C_{20}$-$C_{40}$ alkyl stearates, hydrogenated castor oil, palmitic acid and stearic acid.

Particularly preferred compositions according to the invention are characterized in that the wax component as a constituent of the carrier according to the invention is selected from mixtures of esters of a saturated, monohydric $C_{16}$-$C_{60}$ alkanol and a saturated $C_8$-$C_{36}$ monocarboxylic acid, in particular $C_{20}$-$C_{40}$ alkyl stearate, glycerol triesters of saturated linear $C_{12}$-$C_{30}$ carboxylic acids, which can be hydroxylated, in particular hydrogenated castor oil, and saturated linear $C_{14}$-$C_{36}$ carboxylic acids, in particular palmitic acid and stearic acid.

Other preferred compositions according to the invention are characterized in that the wax component/s as a constituent of the carrier according to the invention is contained in a total quantity of 1-10 wt. %, preferably 1.5-8 wt. %, particularly preferably 2-6 wt. %, extraordinarily preferably 3-5 wt. %, based on the overall composition.

Other preferred compositions according to the invention are characterized in that at least one wax component with a melting point in the range of 25-50° C., selected from coconut fatty acid glycerol mono-, di- and triesters, *Butyrospermum parkii* (shea butter) and esters of saturated, monohydric $C_8$-$C_{18}$ alcohols with saturated $C_{12}$-$C_{18}$ monocarboxylic acids and mixtures of these substances, is contained. These lower melting-point wax components enable the consistency of the product to be optimized and the visible residues on the skin to be minimized. Particularly preferred are commercial products with the INCI name Cocoglycerides, particularly preferably a mixture of $C_{12}$-$C_{18}$ mono-, di- and triglycerides, which melts in the range of 30-32° C., as available for example with the trade name Novata® AB from Cognis, and the products from the Softisan range (Sasol Germany GmbH) with the INCI name Hydrogenated Cocoglycerides, in particular Softisan 100, 133, 134, 138, 142. Other preferred esters of saturated, monohydric $C_{12}$-$C_{18}$ alcohols with saturated $C_{12}$-$C_{18}$ monocarboxylic acids are stearyl laurate, cetearyl stearate (e.g. Crodamol® CSS), stearyl stearate (e.g. Estol 3706), cetyl palmitate (e.g. Cutina® CP, melting point: 46-50° C.) and myristyl myristate (e.g. Cetiol® MM, melting point: 38-42° C.).

Other preferred compositions according to the invention are characterized in that at least one wax component with a melting point in the range of 25-50° C. is contained in a total quantity of 0.01 to 10 wt. %, preferably 0.5-8 wt. %, particularly preferably 1-7.5 wt. % and extraordinarily preferably 1.8-7 wt. %, further preferably 1.9, 2.0, 2.1, 2.2, 2.3, 2.4, 2.5, 3, 3.5, 4, 4.5, 5, 5.5, 6 and 6.5 wt. %, based on the overall composition.

Other preferred compositions according to the invention are characterized in that they contain, for example for improving the consistency and the sensory properties, at least one solid, water-insoluble, particulate filler. In an extraordinarily preferred embodiment, this filler is selected from optionally modified starches (e.g. from maize, rice, potatoes) and starch derivatives, which are optionally pregelatinized, silicon dioxide, silicas, e.g. Aerosil® grades, spherical polyalkyl sesquisiloxane particles (in particular Aerosil® R972 and Aerosil® 200V from Degussa), silica gels, talcum, kaolin, magnesium aluminum silicates, boron nitride, lactoglobulin derivatives, e.g. sodium $C_{8-16}$ isoalkylsuccinyl lactoglobulin sulfonate, obtainable from Brooks Industries as the commercial product Biopol® OE, glass powders, polymer powders, in particular of polyolefins, polycarbonates, polyurethanes, polyamides, e.g. nylon, polyesters, polystyrenes, polyacrylates, (meth)acrylate or (meth)acrylate-vinylidene copolymers, which can be crosslinked, or silicones, and mixtures of these substances.

Polymer powders based on a polymethacrylate copolymer are obtainable e.g. as the commercial product Polytrap® 6603 (Dow Corning). Other polymer powders, e.g. based on polyamides, are obtainable with the name Orgasol® 1002 (polyamide 6) and Orgasol® 2002 (polyamide 12) from Elf Atochem. Other polymer powders, which are suitable as preferred fillers according to the invention, are e.g. polymethacrylates (Micropearl® M from SEPPIC or Plastic Powder A from NIKKOL), styrene-divinylbenzene copolymers (Plastic Powder FP from NIKKOL), polyethylene and polypropylene powders (ACCUREL® EP 400 from AKZO) or also silicone polymers (Silicone Powder X2-1605 from Dow Corning).

Preferred compositions according to the invention are characterized in that they contain at least one solid, water-insoluble, particulate filler in a total quantity of 1 to 99 wt. %, preferably 2-90 wt. %, particularly preferably 3-15 wt. %, extraordinarily preferably 4, 5, 6, 7, 8, 9, 10, 11, 12, 13 and 14 wt. %, based in each case on the overall composition.

Other preferred compositions according to the invention contain at least one oil-in-water emulsifier. Preferred oil-in-water emulsifiers have an HLB value of more than 7. Other preferred oil-in-water emulsifiers are non-ionic. These are emulsifiers that are generally known to the person skilled in the art, as listed for example in Kirk-Othmer, "Encyclopedia of Chemical Technology", 3rd ed., 1979, volume 8, pages 913-916. For ethoxylated products, the HLB value is calculated by the formula HLB=(100−L):5, wherein L is the proportion by weight of lipophilic groups, i.e. the fatty alkyl or fatty acyl groups, in the ethylene oxide adducts, expressed as a percentage by weight.

For the selection of non-ionic oil-in-water emulsifiers that are suitable according to the invention, it is particularly preferred to use a mixture of non-ionic oil-in-water emulsifiers to allow optimum adjustment of the properties of the compositions according to the invention, such as active substance release or washability. The individual emulsifier components in this case provide a proportion of the overall HLB value or average HLB value of the oil-in-water emulsifier mixture according to their quantitative proportion in the total quantity of oil-in-water emulsifiers. In another preferred embodiment, however, the compositions according to the invention, in particular the deodorant or antiperspirant sticks, can also contain only a single oil-in-water emulsifier, preferably with an HLB value in the range from 11-17, particularly preferably 12-15 and extraordinarily preferably 13-14.

Preferred cosmetic compositions according to the invention are characterized in that the non-ionic oil-in-water emulsifiers are selected from ethoxylated $C_8$-$C_{24}$ alkanols with an average of 10-100 moles of ethylene oxide per mole, ethoxylated $C_8$-$C_{24}$ carboxylic acids with an average of 10-100 moles of ethylene oxide per mole, sorbitan monoesters of linear saturated and unsaturated $C_{12}$-$C_{30}$ carboxylic acids ethoxylated with an average of 20-100 moles of ethylene oxide per mole, which can be hydroxylated, in particular those of myristic acid, palmitic acid, stearic acid or of mixtures of these fatty acids, silicone copolyols with ethylene oxide units or with ethylene oxide and propylene oxide units, alkyl mono- and oligoglycosides with 8 to 22 carbon atoms in the alkyl residue and the ethoxylated analogs thereof, ethoxylated sterols, partial esters of polyglycerols with n=2 to 10 glycerol units and esterified with 1 to 4 saturated or unsaturated, linear or branched, optionally hydroxylated $C_8$-$C_{30}$ fatty acid residues, insofar as they have an HLB value of more than 7, and mixtures of the aforementioned substances.

The ethoxylated $C_8$-$C_{24}$ alkanols have the formula $R^1O(CH_2CH_2O)_nH$, wherein $R^1$ denotes a linear or branched alkyl and/or alkenyl residue with 8-24 carbon atoms and n is the average number of ethylene oxide units per molecule, for numbers from 10-100, preferably 10-30 moles of ethylene oxide to 1 mole of caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and technical mixtures thereof. Adducts of 10-100 moles of ethylene oxide to technical fatty alcohols with 12-18 carbon atoms, such as for example coconut, palm, palm kernel or tallow fatty alcohol, are also suitable.

The ethoxylated $C_8$-$C_{24}$ carboxylic acids have the formula $R^1O(CH_2CH_2O)_nH$, wherein $R^1O$ denotes a linear or branched saturated or unsaturated acyl residue with 8-24 carbon atoms and n is the average number of ethylene oxide units per molecule, for numbers from 10-100, preferably 10-30 moles of ethylene oxide to 1 mole of caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselic acid, arachic acid, gadoleic acid, behenic acid, erucic acid and brassidic acid and technical mixtures thereof. Adducts of 10-100 moles of ethylene oxide to technical fatty acids with 12-18 carbon atoms, such as for example coconut, palm, palm kernel or tallow fatty acid, are also suitable. Particularly preferred are PEG-40 monostearate, PEG-50 monostearate, PEG-100 monostearate, PEG-50 monooleate, PEG-100 monooleate, PEG-50 monolaurate and PEG-100 monolaurate.

The $C_{12}$-$C_{18}$ alkanols or the $C_{12}$-$C_{18}$ carboxylic acids with in each case 10-30 units of ethylene oxide per molecule and mixtures of these substances are particularly preferably used, in particular Ceteth-10, Ceteth-12, Ceteth-20, Ceteth-30, Steareth-10, Steareth-12, Steareth-20, Steareth-30, Ceteareth-10, Ceteareth-12, Ceteareth-20, Ceteareth-30, Laureth-12 and Beheneth-20. Preferred sorbitan monoesters of linear saturated and unsaturated $C_{12}$-$C_{30}$ carboxylic acids, ethoxylated with an average of 20-100 moles of ethylene oxide per mole, which may be hydroxylated, are selected from Polysorbate-20, Polysorbate-40, Polysorbate-60 and Polysorbate-80.

Furthermore, $C_8$-$C_{22}$ alkyl mono- and oligoglycosides are preferably used. $C_8$-$C_{22}$ alkyl mono- and oligoglycosides represent known, commercial surfactants and emulsifiers. They are produced in particular by reacting glucose or oligosaccharides with primary alcohols having 8-22 carbon atoms. With regard to the glycoside residue, it is the case that both monoglycosides, in which a cyclic sugar residue is glycosidically bonded to the fatty alcohol, as well as oligomeric glycosides with a degree of oligomerization up to about 8, preferably 1-2, are suitable. The degree of oligomerization here is a statistical average, which is based on a homolog distribution that is conventional for technical products of this type. Products which are obtainable with the trade mark Plantacare® contain a glucosidically bonded $C_8$-$C_{16}$ alkyl group on an oligoglucoside residue, the average degree of oligomerization of which is 1-2, in particular 1.2-1.4. Particularly preferred $C_8$-$C_{22}$ alkyl mono- and oligoglycosides are selected from octyl glucoside, decyl glucoside, lauryl glucoside, palmityl glucoside, isostearyl glucoside, stearyl glucoside, arachidyl glucoside and behenyl glucoside and mixtures thereof. The acyl glucamides which are derived from glucamine are also suitable as non-ionic oil-in-water emulsifiers. Ethoxylated sterols, in particular ethoxylated soy sterols, represent suitable oil-in-water emulsifiers according to the invention. The degree of ethoxylation must be greater than 5, preferably at least 10, in order to have an HLB value greater than 7. Suitable commercial products are e.g. PEG-10 Soy Sterol, PEG-16 Soy Sterol and PEG-25 Soy Sterol.

Furthermore, partial esters of polyglycerols having 2 to 10 glycerol units and esterified with 1 to 4 saturated or unsaturated, linear or branched, optionally hydroxylated $C_8$-$C_{30}$ fatty acid residues are preferably used, provided that they have an HLB value of more than 7. Diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol trieaprate, decaglycerol trilaurate, decaglycerol trimyristate, decaglycerol triisostearate, decaglycerol tristearate, decaglycerol trioleate and decaglycerol trihydroxystearate are particularly preferred.

Other preferred oil-in-water emulsifiers according to the invention are selected from organosiloxane-oxyalkylene copolymers. Preferred organosiloxane-oxyalkylene copolymer O/W emulsifiers are selected from compounds of the general structural formulae (I), (II), (III), (IV) and (V),

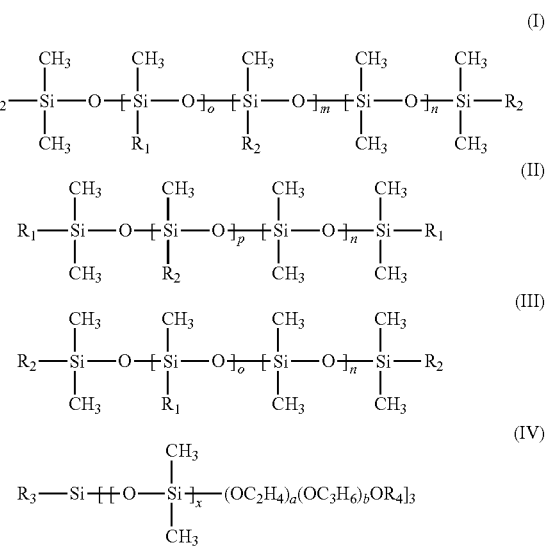

-continued

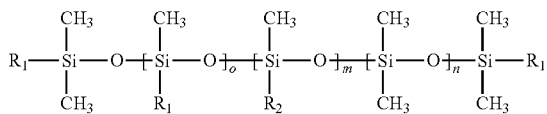
(V)

wherein
the residues $R^1$, independently of one another, represent a linear or branched $C_1$-$C_{30}$ alkyl group or an optionally substituted phenyl group,
the residues $R^2$, independently of one another, represent the groups —$C_cH_{2c}$—O—$(C_2H_4O$—$)_a(C_3H_6O$—$)_bR^5$ or —$C_cH_{2c}$—O—$(C_2H_4O$—$)_aR^5$,
the residues $R^3$ and $R^4$, independently of one another, represent a linear or branched $C_1$-$C_{16}$ alkyl group and preferably methyl groups,
the residues $R^5$, independently of one another, represent a hydrogen atom or a linear or branched $C_1$-$C_{16}$ alkyl group and preferably a hydrogen atom or a methyl group,
m represents a number from 0-20,
n represents a number from 0-500,
o represents a number from 0-20,
p represents a number from 1-50,
a represents a number from 0-50,
b represents a number from 0-50,
a+b are at least 1,
c represents a number from 1-4, particularly preferably 3,
x represents a number from 1-100.

Preferred compositions according to the invention are characterized in that at least one organosiloxane-oxyalkylene copolymer of the general structural formula (II) is contained with
$R^1$=methyl,
$R^2$=—$C_cH_{2c}$—O—$(C_2H_4O$—$)_a(C_3H_6O$—$)_bR^5$
with
a=18
b=18
c=3
$R^5$=methyl,
n=10-500,
p=10-50.

An organosiloxane-oxyalkylene copolymer of this type is available for example with the trade name Dow Corning 190 (INCI: PEG/PPG-18/18 Dimethicone).

Other preferred compositions according to the invention are characterized in that at least one organosiloxane-oxyalkylene copolymer of the general structural formula (II) is contained with
$R^1$=methyl,
$R^2$=—$C_c$—$H_{2c}$—O—$(C_2H_4O$—$)_a(C_3H_6O$—$)_bR^5$
with
a=12
b=0
c=3
$R^5$=methyl,
n=10-500,
p=10-50.

An organosiloxane-oxyalkylene copolymer of this type is available for example with the trade name Dow Corning 193 (INCI: PEG-12 Dimethicone).

Other preferred compositions according to the invention are characterized in that at least one organosiloxane-oxyalkylene copolymer of the general structural formula (II) is contained with
$R^1$=methyl,
$R^2$=—$C_c$—$H_{2c}$—O—$(C_2H_4O$—$)_a(C_3H_6O$—$)_bR^5$
with
a=7
b=0
c=2
$R^5$=methyl,
n=0
p=1.

An organosiloxane-oxyalkylene copolymer of this type is available for example with the trade name Silwet L-77.

Other preferred compositions according to the invention are characterized in that at least one organosiloxane-oxyalkylene copolymer of the general structural formula (II) is contained with
$R^1$=methyl,
$R^2$=—$C_cH_{2c}$O—$(C_2H_4O$—$)_a(C_3H_6O$—$)_bR^5$
with
a=22
b=24
c=3
$R^5$=methyl,
n=10-500,
p=10-50.

An organosiloxane-oxyalkylene copolymer of this type is available for example in a mixture with cyclomethicone with the trade name Mirasil DMCO (INCI: Cyclomethicone, PEG/PPG-22/24 Dimethicone).

Other preferred compositions according to the invention are characterized in that at least one organosiloxane-oxyalkylene copolymer of the general structural formula (II) is contained with
$R^1$=methyl,
$R^2$=—$C_cH_{2c}$—O—$(C_2H_4O$—$)_a(C_3H_6O$—$)_bR^5$
with
a=17
b=18
c=3
$R^5$=methyl,
n=10-500,
p=10-50.

An organosiloxane-oxyalkylene copolymer of this type is available for example with the trade name Dow Corning Q2-5220 (INCI: PEG/PPG-17/18 Dimethicone).

Other preferred compositions according to the invention are characterized in that at least one organosiloxane-oxyalkylene copolymer of the general structural formula (II) is contained with
$R^1$=methyl,
$R^2$=—$C_cH_{2c}$—O—$(C_2H_4O$—$)_a(C_3H_6O$—$)_bR^5$
with
a=20
b=6
c=3
$R^5$=methyl,
n=10-500,
p=5-50.

An organosiloxane-oxyalkylene copolymer of this type is available for example with the trade name Abil B 88184 (INCI: PEG/PPG-20/6 Dimethicone).

Other preferred compositions according to the invention are characterized in that at least one organosiloxane-oxyalkylene copolymer of the general structural formula (II) is contained with
$R^1$=methyl,
$R^2$=—$C_cH_{2c}$—O—$(C_2H_4O$—$)_a(C_3H_6O$—$)_bR^5$
with a=14
b=4
c=3
$R^5$=methyl,
n=10-500,
p=5-50.

An organosiloxane-oxyalkylene copolymer of this type is available for example with the trade name Abil B 8851 (INCI: PEG/PPG-14/4 dimethicone).

Particularly preferred compositions according to the invention, which are made up as a water-free wax stick, water-free soft solid or water-free cream, are characterized in that at least one oil-in-water emulsifier, preferably at least one non-ionic oil-in-water emulsifier, is contained in a total quantity of 0.5-10 wt. %, preferably 1-9 wt. %, particularly preferably 1.5-8.5 wt. %, extraordinarily preferably 2-8 wt. %, and further also 2.5, 3, 3.5, 4, 4.5, 5, 5.5, 6, 6.5, 7, 7.5 and 8 wt. %, based on the overall composition.

Other preferred compositions according to the invention are characterized in that they are formulated as a dibenzylidene alditol-based gel, in particular as a dibenzylidene sorbitol-based gel. Corresponding gels, which are generally so solid that they are marketed as a stick, are disclosed for example in U.S. Pat. No. 5,705,171, U.S. Pat. No. 5,939,055, U.S. Pat. No. 5,725,846, EP 812183 and EP 1269977. As the carrier, an anhydrous polyhydric alcohol with 3 to 9 carbon atoms is used, which is liquid under normal conditions. These include 1,2-propylene glycol, 2-methyl-1,3-propanediol, glycerol, 1,2-butylene glycol, 1,3-butylene glycol and 1,4-butylene glycol, pentylene glycols such as 1,2-pentanediol and 1,5-pentanediol, hexanediols such as 1,2-hexanediol and 1,6-hexanediol, hexanetriols such as 1,2,6-hexanetriol, 2-ethyl-2-hydroxymethyl-1,3-propanediol, diethylene glycol, triethylene glycol, dipropylene glycol, tripropylene glycol, diglycerol and triglycerol. 1,2-Propylene glycol is particularly preferred. 1,2-Propylene glycol which makes up 70-95 wt. %, preferably 75-92 wt. %, of the total weight of the stick is extraordinarily preferred. This solvent is gelled with a dibenzylidene alditol, in particular with dibenzylidene sorbitol (DBS). Also suitable as gelling agents with a similar texture are dibenzylidene xylitol and dibenzylidene ribitol, with DBS being preferred. This gelling agent is added preferably in a total quantity of 0.3-2 wt. %, particularly preferably 0.5-1.8 wt. %, extraordinarily preferably 0.8-1.5 wt. %, based on the total weight of the composition.

The dibenzylidene alditol-based gels are particularly preferably transparent. In another preferred embodiment, further additives, such as in particular active antiperspirant or deodorant substances, oils, emulsifiers and of course the active substance capsules according to the invention, are selected so as not to impair the transparency of the end product.

Dibenzylidene alditol-based gels according to the invention also contain preferably at least one active antiperspirant substance, particularly preferably in a total quantity of 3-27 wt. %, preferably 5-22 wt. % and particularly preferably 10-20 wt. %, based in each case on the total weight of the water of crystallization-free active substance (USP) in the overall composition. The at least one active antiperspirant substance is particularly preferably present in dissolved or solubilized form in the propylene glycol carrier of the dibenzylidene alditol-based gel.

Dibenzylidene alditol-based gels preferably also contain at least one cosmetic oil. In principle, all of the above-mentioned oils are suitable. In terms of skin feel and transparency, preferred oils are selected from the addition products of 1 to 5 propylene oxide units to mono- or polyhydric $C_{8-22}$ alkanols such as octanol, decanol, decanediol, lauryl alcohol, myristyl alcohol and stearyl alcohol, e.g. PPG-2 myristyl ether and PPG-3 myristyl ether, and the addition products of at least 6 ethylene oxide and/or propylene oxide units to mono- or polyhydric $C_{3-22}$ alkanols, such as glycerol, butanol, butanediol, myristyl alcohol and stearyl alcohol, which may be esterified if desired, e.g. PPG-14 butyl ether, PPG-9 butyl ether, PPG-10 butanediol, PPG-15 stearyl ether and glycereth-7 diisononanoate.

Other preferred oils are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

The at least one oil is preferably added in a total quantity of 0.1-5 wt. %, particularly preferably 0.5-3 wt. %, extraordinarily preferably 0.8-1.5 wt. %, based on the total weight of the dibenzylidene alditol-gelled composition.

Preferred dibenzylidene alditol-based gels according to the invention contain as an additional gel-forming agent at least one substance selected from the group encompassing cellulose ethers, especially hydroxyalkyl celluloses, in particular hydroxypropyl cellulose, hydroxypropyl methyl cellulose, hydroxyethyl cellulose, carboxymethyl cellulose, cetyl hydroxyethyl cellulose, hydroxybutyl methyl cellulose, methyl hydroxyethyl cellulose, and also xanthan gum, sclerotium gum, succinoglucans, polygalactomannans, in particular guar gums and locust bean gum, in particular guar gum and locust bean gum themselves and the non-ionic hydroxyalkyl guar derivatives and locust bean gum derivatives, such as hydroxypropyl guar, carboxymethyl hydroxypropyl guar, hydroxypropyl methyl guar, hydroxyethyl guar and carboxymethyl guar, and also pectins, agar, carrageen (carrageenan), tragacanth, gum arabic, karaya gum, tara gum, gellan, gelatin, casein, propylene glycol alginate, alginic acids and salts thereof, in particular sodium alginate, potassium alginate and calcium alginate. Hydroxypropyl cellulose is particularly preferred according to the invention. This additional gel-forming agent is preferably contained in a total quantity of 0.08-1 wt. %, preferably 0.1-0.5 wt. %, particularly preferably 0.2-0.4 wt. %, extraordinarily preferably 0.3 wt. %, based in each case on the total weight of the composition.

In another preferred embodiment, the dibenzylidene alditol-based gels according to the invention contain at least one complexing agent. Particularly preferred as complexing agents are anhydrous ethylenediaminetetraacetic acid (EDTA) and its sodium salts, in particular the tetrasodium salt and the trisodium salt, anhydrous 1,3-propylenediaminetetraacetic acid (PDTA) and its sodium salts, in particular the tetrasodium salt and the trisodium salt, anhydrous hydroxyethyl-ethylenediaminetetraacetic acid (HEDTA) and its sodium salts, in particular the tetrasodium salt and the trisodium salt, anhydrous diethylenetriaminepentaacetic acid (DTPA) and its sodium salts, in particular the pentasodium salt, the tetrasodium salt and the trisodium salt, nitrilotriacetic acid (NTA) and its sodium salts, β-alanine diacetic acid and its salts, ethanol diglycine disodium salt, diethanol glycine sodium salt and phosphonic acids and their salts. The at least one complex-forming substance is preferably contained in a total quantity of 0.05-2 wt. %, particularly preferably 0.1-1, extraordinarily preferably 0.2-0.5 wt. %, based on the total weight of the composition according to the invention.

In another preferred embodiment, the dibenzylidene alditol-based gels according to the invention contain at least one oil-in-water emulsifier. Preferred oil-in-water emulsifiers, in particular preferred non-ionic oil-in-water emulsifiers, are already described above.

Particularly preferred dibenzylidene alditol-based gel compositions according to the invention are characterized in that at least one oil-in-water emulsifier, preferably at least one non-ionic oil-in-water-emulsifier, is contained in a total quantity of 0.1-5 wt. %, preferably 0.2-3 wt. %, particularly preferably 0.3-2 wt. %, extraordinarily preferably 0.4-1 wt. %, further preferably also 0.5, 0.6, 0.7, 0.8 and 0.9 wt. %, based on the overall composition.

The form in which the compositions according to the invention are made up is preferably directed towards the requirements of the desired application.

The compositions according to the invention are preferably present in the form of a suspension, i.e. the active antiperspirant substance and optionally other insoluble components are suspended in a liquid carrier.

In a preferred embodiment according to the invention, the compositions according to the invention are made up as a non-sprayable suspension. A disperse system of this type should be shaken before application.

The suspension described above is thickened or solidified to form a stick in another preferred embodiment.

Preferred compositions according to the invention are packaged e.g. in roll-on dispensers or stick dispensers.

The form in which compositions according to the invention, which are applied as a non-aerosol, are made up is preferably directed towards the requirements of the type of application.

Preferred compositions according to the invention are present in the form of a solid, semi-solid, liquid, dispersion, water-free emulsion, suspension or gel.

In a particularly preferred embodiment, the compositions according to the invention are present in liquid form. The term "liquid" within the meaning of the invention also includes any dispersions of solids in liquids. Compositions according to the invention can also be present as pastes, ointments, lotions or creams. Solid compositions can be present, for example, as a loose powder, pressed powder or as a stick.

The application can, e.g. in the case of liquid agents, preferably also take place with a roll-on applicator, as is known e.g. from the sector of the roll-on deodorants. These roll-ons have a ball supported in a ball bed, which can be moved over a surface by means of movement. During this process, the ball takes up some of the agent to be distributed and transports it onto the surface to be treated.

The agents according to the invention, preferably liquid agents, can also be multi-phase; the phases can be arranged, for example, horizontally, i.e. one on top of the other, or vertically, i.e. adjacent to one another. It can also be a disperse system, in which e.g. the solid components are distributed inhomogeneously in the liquid matrix, so that a disperse system of this type has to be shaken before application.

Antiperspirant sticks on a water-free basis can be present in gel form, in which case the oil phase can contain at least one silicone component or consist of at least one silicone component. Furthermore, the compositions according to the invention which are formulated as antiperspirant sticks can be present on a water-free fat basis, on the basis of a polyol-in-oil emulsion, on the basis of an oil-in-polyol emulsion, on the basis of a polyol-oil multiple emulsion, on the basis of a nanoemulsion and on the basis of a microemulsion, in which case the polyol phase is water-free. Gel sticks can be formulated on the basis of alditols, in particular dibenzylidene sorbitol, N-acyl amino acid amides, 12-hydroxystearic acid, polyamides and polyamide derivatives.

Water-free antiperspirant wax sticks contain about 30-70 wt. % of at least one cosmetic oil which is liquid under normal conditions, about 15-25 wt. % of a fatty component which is solid under normal conditions, of which the greatest part generally has a melting point of approx. 50° C., or generally consists of fatty alcohols, in particular of stearyl alcohol, but also cetyl alcohol and optionally also arachidyl alcohol and/or behenyl alcohol, while a smaller portion—about 0.5-5 wt. %—consists of at least one fatty component with a melting point of approx. 55-120° C. In addition, 0.5-8 wt. % of at least one fatty component with a melting point of approx. 25-35° C. can be contained. Furthermore, 0.5-30 wt. % of at least one filler can be contained, which is typically selected from talcum, cellulose powders, starches and starch derivatives. Furthermore, 0.1-10 wt. %, preferably 1-5 wt. %, particularly preferably 2-4 wt. % of at least one oil-in-water emulsifier can be contained.

A preferred embodiment according to the invention as a water-free antiperspirant wax stick is characterized by the following ingredients:

5-40 wt. %, preferably 10-35 wt. %, particularly preferably 11-28 wt. % and extraordinarily preferably 12-20 wt. % (USP) of at least one active antiperspirant substance, 30-70 wt. % of at least one cosmetic oil which is liquid under normal conditions, 15-32 wt. % of a fatty component which is solid under normal conditions, of which more than 65 wt. %, preferably more than 70 wt. %, particularly preferably more than 80 wt. %, based in each case on the total content of fatty components which are solid under normal conditions, consists of $C_{16}$-$C_{30}$ fatty alcohols, preferably selected from the group consisting of stearyl alcohol, cetyl alcohol and mixtures thereof, wherein, in addition to stearyl alcohol and/or cetyl alcohol, also 0.1-3 wt. %, based on the total stick, of arachidyl alcohol and/or behenyl alcohol and/or at least one $C_{24}$-$C_{30}$ fatty alcohol is/are particularly preferably contained, also 0.5-5 wt. %, based on the total stick, of at least one fatty component with a melting point of 75-120° C. and 0.5-8 wt. %, based on the total stick, of at least one fatty component with a melting point of 25-45° C., and also 0.5-30 wt. %, preferably 1-25 wt. %, particularly preferably 5-20 wt. %, extraordinarily preferably 10-15 wt. %, of at least one filler, which is particularly preferably selected from talcum, cellulose powders, starches and starch derivatives.

All of the quantitative data relate, unless otherwise specified, to the weight of the composition according to the invention.

In a particularly preferred embodiment according to the invention, the water-free antiperspirant wax stick is present as a so-called multi-phase stick, in particular as a two-phase stick. These are understood according to the invention to be sticks which, for example, contain a first wax stick phase as the core and at least a second wax stick phase as a ring around the first phase. In addition to a concentric, annular arrangement of the individual phases, other arrangements are also possible, in particular an arrangement in strip form. The individual phases can, for example, be differentiated from one another by different colors, but also by different components. Corresponding multi-phase sticks are disclosed, for example, in U.S. Pat. No. 6,936,242 and WO 00/67712 A1. Preferred production methods for these types of sticks are disclosed in U.S. Pat. No. 6,838,032.

A configuration as a multi-phase stick, in particular as a two-phase stick, in which only one of the phases contains a particular active substance, is particularly preferred.

The application can also take place e.g. with substrates which are loaded with a preparation according to the invention. Particularly preferred are wet wipes, i.e. wet wipes pre-prepared individually packaged, as are well known e.g. from the area of glass cleaning (spectacle cleaning wipes) or from the area of moist toilet tissues. These wet wipes, which can preferably also contain preservatives, are then impregnated or loaded with an agent according to the invention. They can be used e.g. as an antiperspirant wipe, which is of particular interest for use when traveling. It may be particularly preferred if these wipes are individually packaged.

Preferred substrate materials are selected from flat wipes. They can consist of a fibrous or cellular, flexible material which has adequate mechanical stability together with softness for application to the skin. These wipes include wipes made of woven and nonwoven, synthetic and natural fibers, felt, paper or foam, such as hydrophilic polyurethane foam.

Conventional wipes made of nonwoven material (nonwovens) are preferably used here. Nonwovens are in general defined as adhesively bonded, fibrous products which have a mat or layered fiber structure, or those which comprise fiber mats in which the fibers are distributed randomly or in a statistical arrangement. The fibers may be natural, such as cellulose, lyocell, wool, silk, jute, hemp, cotton, linen, sisal or ramie; or synthetic, such as rayon, cellulose ester, polyvinyl derivatives, polyolefins, polyamides or polyester. In general, any fiber diameter or titer is suitable for the present invention. The nonwoven materials used here tend, owing to the random or statistical arrangement of fibers in the nonwoven material, which impart excellent strength in all directions, not to tear or disintegrate. Examples of nonwoven materials that are suitable as substrates in the present invention are known, for example, from WO 98/18441. Preferred porous and flat cleaning wipes consist of one or various fibrous materials, in particular of cotton, finished cotton, polyamide, polyester or mixtures of these. The substrates in the form of wipes preferably have an area of 10 to 5000 cm$^2$, preferably 50 to 2000 cm$^2$, in particular 100 to 1500 cm$^2$ and particularly preferably 200 to 1000 cm$^2$. The weight per unit area or base weight of the material here is generally between 20 and 1000 g/m$^2$, preferably from 30 to 500 g/m$^2$ and in particular from 50 to 150 g/m$^2$. Preferred deodorizing substrates according to the invention can be obtained by dipping or impregnating or also by melting the composition according to the invention onto a substrate.

Fragrances and perfumes are not included according to the invention in the cosmetic oils that are taken into account when calculating the proportion by weight of the carrier oils b) described above. Examples of fragrance and perfume compounds of the esters type are benzyl acetate, phenoxyethyl isobutyrate, p-tert.-butyl cyclohexyl acetate, linalyl acetate, dimethyl benzyl carbinyl acetate (DMBCA), phenyl ethyl acetate, benzyl acetate, ethyl methyl phenyl glycinate, allyl cyclohexyl propionate, styrallyl propionate, benzyl salicylate, cyclohexyl salicylate, Floramat, Melusat and Jasmecyclat. Examples of fragrance and perfume compounds of the ethers type are benzyl ethyl ether and Ambroxan; examples of fragrance and perfume compounds of the aldehydes type are the linear alkanals with 8-18 C atoms, citral, citronellal, citronellyl oxyacetaldehyde, cyclamen aldehyde, lilial and bourgeonal; examples of fragrance and perfume compounds of the ketones type are the ionones, alpha-isomethyl ionone and methyl cedryl ketone; examples of fragrance and perfume compounds of the alcohols type are anethole, citronellol, eugenol, geraniol, linalool, phenyl ethyl alcohol and terpineol; examples of fragrance and perfume compounds of the terpenes type are limonene and pinene. Examples of fragrance and perfume compounds are pine oil, citrus oil, jasmine oil, patchouli oil, rose oil, ylang-ylang oil, clary sage oil, chamomile oil, clove oil, mint oil, cinnamon leaf oil, lime blossom oil, juniper berry oil, vetiver oil, olibanum oil, galbanum oil, labdanum oil, orange blossom oil, neroli oil, orange-peel oil and sandalwood oil, as well as the essential oils such as angelica root oil, anise oil, arnica blossom oil, basil oil, bay oil, bergamot oil, champaca flower oil, silver fir oil, silver fir cone oil, elemi oil, eucalyptus oil, fennel oil, fir needle oil, geranium oil, gingergrass oil, guaiacum oil, gurjun balsam oil, helichrysum oil, ho oil, ginger oil, iris oil, cajeput oil, calamus oil, chamomile oil, camphor oil, canaga oil, cardamom oil, cassia oil, pine-needle oil, copaiva balsam oil, coriander oil, curled mint oil, caraway oil, cumin oil, lavender oil, lemongrass oil, lime oil, mandarin oil, melissa oil, musk seed oil, myrrh oil, clove oil, niaouli oil, orange oil, oregano oil, palmarosa oil, patchouli oil, Peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, juniper berry oil, wormwood oil, wintergreen oil, hyssop oil, cinnamon oil, citronella oil, lemon oil and cypress oil. Other fragrance and perfume compounds are ambrettolide, $\alpha$-amyl cinnamaldehyde, anethole, anisaldehyde, anisyl alcohol, anisole, methyl anthranilate, acetophenone, benzyl acetone, benzaldehyde, ethyl benzoate, benzophenone, benzyl alcohol, benzyl acetate, benzyl benzoate, benzyl formate, benzyl valerianate, borneol, bornyl acetate, $\alpha$-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl n-amyl ketone, methyl anthranilic acid methyl ester, p-methyl acetophenone, methyl chavicol, p-methyl quinoline, methyl $\beta$-naphthyl ketone, methyl n-nonyl acetaldehyde, methyl n-nonyl ketone, muscone, $\beta$-naphthol ethyl ether, $\beta$-naphthol methyl ether, nerol, nitrobenzene, n-nonyl aldehyde, nonyl alcohol, n-octyl aldehyde, p-oxyacetophenone, pentadecanolide, $\beta$-phenyl ethyl alcohol, phenyl acetaldehyde dimethyl acetal, phenylacetic acid, pulegone, safrole, isoamyl salicylate, methyl salicylate, hexyl salicylate, cyclohexyl salicylate, santalol, skatole, terpineol, thymene, thymol, $\gamma$-undecalactone, vanillin, veratrum aldehyde, cinnamaldehyde, cinnamyl alcohol, cinnamic acid, ethyl cinnamate and benzyl cinammate.

Other (more readily volatile) perfumes are alkyl isothiocyanates (alkyl mustard oils), butanedione, limonene, linalool, linalyl acetate and propionate, menthol, menthone, methyl n-heptenone, phellandrene, phenyl acetaldehyde, terpinyl acetate, citral and citronellal.

Mixtures of various fragrances are preferably used which together produce an attractive fragrance note.

Suitable perfume oils can also contain natural perfume mixtures as can be obtained from plant or animal sources, e.g. pine, citrus, jasmine, rose, lily or ylang-ylang oils. Essential oils with low volatility, which are mainly used as aroma components, are also suitable as perfume oils, e.g. sage oil, chamomile oil, melissa oil, mint oil, cinnamon leaf oil, lime-blossom oil, juniper berry oil, vetiver oil, olibanum oil, galbanum oil, laudanum oil, clove oil, isoeugenol, thyme oil, bergamot oil, geranium oil and rose oil.

Preferred compositions according to the invention are characterized in that at least one fragrance is contained in a total quantity of 0.1-15 wt. %, preferably 0.5-10 wt. %, particularly preferably 1-8 wt. %, extraordinarily preferably 2-7 wt. %, further extraordinarily preferably 3-6 wt. %, based in each case on the total weight of the composition.

Other preferred compositions according to the invention are characterized by a content of at least one so-called "skin-cooling active substance". Skin-cooling active substances within the meaning of the present application are understood to be active substances which, when applied onto the skin, as a result of surface anaesthetizing and irritation of the cold-sensitive nerves in migraine and the like, produce a pleasant cool sensation, even if the areas of skin being treated actually display a normal or elevated temperature.

Preferred skin-cooling active substances are, in particular, menthol, isopulegol and menthol derivatives, e.g. menthyl lactate, menthyl pyrrolidone carboxylic acid, menthyl methyl ether, menthoxypropanediol, menthone glycerin acetal (9-methyl-6-(1-methylethyl)-1,4-dioxaspiro(4.5)decane-2-methanol), monomenthyl succinate and 2-hydroxymethyl-3,5,5-trimethyl cyclohexanol. Menthol, isopulegol, menthyl lactate, menthoxypropanediol and menthyl pyrrolidone carboxylic acid are particularly preferred as skin-cooling active substances.

Preferred compositions according to the invention contain at least one skin-cooling active substance in total quantities of 0.01-1 wt. %, preferably 0.02-0.5 wt. % and particularly preferably 0.05-0.2 wt. %, based in each case on the total weight of the composition.

Preferred compositions according to the invention are characterized in that at least one encapsulated active substance is contained. The active substances that can advantageously be encapsulated are, in particular, fragrances, perfume oils and/or skin-cooling active substances, but also other active skincare substances, such as vitamins, antioxidants etc.

Water-soluble polymers, such as starch, physically and/or chemically modified starches, cellulose derivatives, such as e.g. carboxymethyl cellulose, methyl cellulose, hydroxyethyl cellulose or hydroxypropyl methyl cellulose, carrageens, alginates, maltodextrins, dextrins, plant gums, pectins, xanthans, polyvinyl acetate and polyvinyl alcohol, polyvinyl pyrrolidine, polyamides, polyesters and homo- and copolymers of monomers selected from acrylic acid, methacrylic acid, maleic acid, fumaric acid, itaconic acid and the esters and salts of these acids, and any mixtures of these polymers, are preferred as the capsule material.

Preferred capsule materials are chemically modified starches, in particular aluminum starch octenylsuccinate, e.g. the commercial product Dry Flo Plus from National Starch, or sodium starch octenylsuccinate, e.g. the commercial product Capsul from National Starch, and also carboxymethyl cellulose, carboxymethyl cellulose, methyl cellulose, hydroxyethyl cellulose and hydroxypropyl methyl cellulose, ethyl cellulose, e.g. the commercial product Tylose H 10 from Clariant, as well as carrageen, alginates and maltodextrins, and any mixtures of these polymers.

In another preferred embodiment according to the invention, the compositions according to the invention contain 0 to no more than 50 wt. %, preferably 1 to 40 wt. %, particularly preferably 2-30 wt. %, extraordinarily preferably 5-15 wt. %, of ethanol. In the case of higher ethanol contents, anhydrous (absolute) ethanol should be used.

Furthermore, the compositions according to the invention can contain additional active deodorant substances. As active deodorant substances, it is possible to use antimicrobial, antibacterial or bacteriostatic substances, antioxidants or odor adsorbants (e.g. zinc ricinoleate). Suitable antimicrobial, antibacterial or bacteriostatic substances are, in particular, organohalogen compounds and organohalides, quaternary ammonium compounds, a series of plant extracts and zinc compounds. Halogenated phenol derivatives are preferred, such as e.g. hexachlorophene or Irgasan DP 300 (triclosan, 2,4,4'-trichloro-2' hydroxydiphenyl ether), 3,4,4'-trichlorocarbonilide, chlorhexidine (1,1'-hexamethylene-bis[5-(4-chlorophenyl)]biguanide), chlorhexidine gluconate, benzalkonium halides and cetylpyridinium chloride. In addition, sodium bicarbonate, sodium phenolsulfonate and zinc phenolsulfonate and e.g. the components of lime blossom oil can be used. Also more weakly effective antimicrobial substances, but which have a specific action against the gram-positive microbes responsible for the decomposition of sweat, can be used as active deodorant substances. Benzyl alcohol can also be used as an active deodorant substance. Other antibacterially effective deodorants are lantibiotics, glycoglycerolipids, sphingolipids (ceramides), sterols and other active substances that inhibit bacterial adhesion to the skin, e.g. glycosidases, lipases, proteases, carbohydrates, di- and oligosaccharide fatty acid esters and alkylated mono- and oligosaccharides. Preferred active deodorant substances are long-chain diols, e.g. 1,2 alkane($C_5$-$C_{18}$)diols, glycerol mono ($C_8$-$C_{18}$) fatty acid esters or, particularly preferably, glycerol mono($C_6$-$C_{16}$)alkyl ethers, in particular 2-ethylhexyl glycerol ether, which are highly compatible with the skin and mucosa and are effective against corynebacteria, and also phenoxyethanol, phenoxyisopropanol (3-phenoxypropan-2-ol), anisyl alcohol, 2-methyl-5-phenylpentan-1-ol, 1,1-dimethyl-3-phenylpropan-1-ol, benzyl alcohol, 2-phenylethan-1-ol, 3-phenylpropan-1-ol, 4-phenylbutan-1-ol, 5-phenylpentan-1-ol, 2-benzylheptan-1-ol, 2-dimethyl-3-phenylpropan-1-ol, 2,2-dimethyl-3-(3 methylphenyl)propan-1-ol, 2-ethyl-3-phenylpropan-1-ol, 2-ethyl-3-(3'-methylphenyl)propan-1-ol, 3-(3'-chlorophenyl)-2-ethylpropan-1-ol, 3-(2'-chlorophenyl)-2-ethylpropan-1-ol, 3-(4'-chlorophenyl)-2-ethylpropan-1-ol, 3-(3',4'-dichlorophenyl)-2-ethylpropan-1-ol, 2-ethyl-3-(T-methylphenyl)propan-1-ol, 2-ethyl-3-(4'-methylphenyl)propan-1-ol, 3-(3',4'-dimethylphenyl)-2-ethylpropan-1-ol, 2-ethyl-3-(4'-methoxyphenyl) propan-1-ol, 3-(3',4'-dimethoxyphenyl)-2-ethylpropan-1-ol, 2-allyl-3-phenylpropan-1-ol and 2-n-pentyl-3-phenylpropan-1-ol.

Complex-forming substances can also support the deodorizing action by forming the heavy metal ions that have an oxidative catalytic action (e.g. iron or copper) into stable complexes. Preferred complexing agents are e.g. the salts of ethylenediaminetetraacetic acid or of nitrilotriacetic acid and the salts of 1-hydroxyethane-1,1-diphosphonic acid.

The composition of some preferred compositions according to the invention can be taken from the following tables (all data in wt. %, based on the total weight of the composition):

|  | 1 | 2 | 3 | 4 |
| --- | --- | --- | --- | --- |
| Active antiperspirant substance (USP) | 5.0 to 40 | 10 to 35 | 15 to 28 | 23 to 27 |
| Liquid oil as carrier | 30 to 95 | 40 to 60 | 45 to 55 | 40 to 55 |
| Free water | 0 to 7 | 0 to 7 | 0 to 3 | 0 to 3 |
| ACTIVATOR-(I)* | 0.01 to 5 | 0.1 to 3 | 0.5 to 2 | 1 to 1.5 |

*wherein $R^1$ is an aliphatic hydrocarbon residue with 1 to 3 C atoms,
$R^2$ is an aliphatic hydrocarbon residue with 8 to 30 C atoms,
m is a rational number from 10 to 50,
n is a rational number from 0 to 10,
p is a rational number from 1 to 10.

| | 5 | 6 | 7 | 8 |
|---|---|---|---|---|
| Antiperspirant aluminum salt (USP) | 5.0 to 40 | 10 to 35 | 15 to 28 | 23 to 27 |
| Liquid oil as carrier | 30 to 95 | 40 to 60 | 45 to 55 | 40 to 55 |
| Free water | 0 to 7 | 0 to 7 | 0 to 3 | 0 to 3 |
| ACTIVATOR-(I)* | 0.01 to 5 | 0.1 to 3 | 0.5 to 2 | 1 to 1.5 |

*wherein $R^1$ is an aliphatic hydrocarbon residue with 1 to 3 C atoms,
$R^2$ is an aliphatic hydrocarbon residue with 8 to 30 C atoms,
m is a rational number from 10 to 50,
n is a rational number from 0 to 10,
p is a rational number from 1 to 10.

| | 9 | 10 | 11 | 12 |
|---|---|---|---|---|
| Antiperspirant aluminum salt (USP) | 5.0 to 40 | 10 to 35 | 15 to 28 | 23 to 27 |
| Liquid oil as carrier | 30 to 95 | 40 to 60 | 45 to 55 | 40 to 55 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |

**wherein $R^1$ is a methyl group,
$R^2$ is an n-decyl group,
m is a rational number from 21 to 23,
n = 0,
p is a rational number from 4 to 8.

| | 13 | 14 | 15 | 16 |
|---|---|---|---|---|
| Antiperspirant aluminum salt (USP) | 5.0 to 40 | 10 to 35 | 15 to 28 | 23 to 27 |
| Liquid oil as carrier | 30 to 95 | 40 to 60 | 45 to 55 | 40 to 55 |
| Free water | 0 to 7 | 0 to 7 | 0 to 3 | 0 to 3 |
| Methoxy PEG-22/Dodecyl Glycol Copolymer | 0.01 to 5 | 0.1 to 3 | 0.5 to 2 | 1 to 1.5 |

| | 17 | 18 | 19 | 20 |
|---|---|---|---|---|
| Antiperspirant aluminum salt (USP) | 5.0 to 40 | 10 to 35 | 15 to 28 | 23 to 27 |
| Volatile cyclic silicone oils (cyclomethicone) | 30 to 95 | 40 to 60 | 45 to 55 | 40 to 55 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |

**wherein $R^1$ is a methyl group,
$R^2$ is an n-decyl group,
m is a rational number from 21 to 23,
n = 0,
p is a rational number from 4 to 8.

| | 21 | 22 | 23 | 24 |
|---|---|---|---|---|
| Antiperspirant aluminum salt (USP) | 5.0 to 40 | 10 to 35 | 15 to 28 | 23 to 27 |
| Volatile cyclic silicone oils (cyclomethicone) | 30 to 95 | 40 to 60 | 45 to 55 | 40 to 55 |
| Free water | 0 to 7 | 0 to 7 | 0 to 3 | 0 to 3 |
| Methoxy PEG-22/Dodecyl Glycol Copolymer | 0.01 to 5 | 0.1 to 3 | 0.5 to 2 | 1 to 1.5 |

| | 25 | 26 | 27 | 28 |
|---|---|---|---|---|
| Antiperspirant aluminum salt (USP) | 5.0 to 40 | 10 to 35 | 15 to 28 | 23 to 27 |
| Volatile linear polydimethyl siloxanes with 2 to 10 siloxane units | 30 to 95 | 40 to 60 | 45 to 55 | 40 to 55 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |

**wherein $R^1$ is a methyl group,
$R^2$ is an n-decyl group,
m is a rational number from 21 to 23,
n = 0,
p is a rational number from 4 to 8.

| | 29 | 30 | 31 | 32 |
|---|---|---|---|---|
| Antiperspirant aluminum salt (USP) | 5.0 to 40 | 10 to 35 | 15 to 28 | 23 to 27 |
| Volatile linear polydimethyl siloxanes with 2 to 10 siloxane units | 30 to 95 | 40 to 60 | 45 to 55 | 40 to 55 |
| Free water | 0 to 7 | 0 to 7 | 0 to 3 | 0 to 3 |
| Methoxy PEG-22/Dodecyl Glycol Copolymer | 0.01 to 5 | 0.1 to 3 | 0.5 to 2 | 1 to 1.5 |

| | 33 | 34 | 35 | 36 |
|---|---|---|---|---|
| Antiperspirant aluminum salt (USP) | 5.0 to 40 | 10 to 35 | 15 to 28 | 23 to 27 |
| i) ester oil, selected from 2-ethylhexyl palmitate, isopropyl myristate and isopropyl palmitate, and ii) at least one isoparaffin oil, selected from isodecane, isoundecane, isododecane, isotridecane, isotetradecane, isopentadecane, isohexadecane and isoeicosane, and iii) 0 - no more than 1 wt. % cyclomethicone | 30 to 95 | 40 to 60 | 45 to 55 | 40 to 55 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |

**wherein $R^1$ is a methyl group,
$R^2$ is an n-decyl group,
m is a rational number from 21 to 23,
n = 0,
p is a rational number from 4 to 8.

| | 37 | 38 | 39 | 40 |
|---|---|---|---|---|
| Antiperspirant aluminum salt (USP) | 5.0 to 40 | 10 to 35 | 15 to 28 | 23 to 27 |
| i) ester oil, selected from 2-ethylhexyl palmitate, isopropyl myristate and isopropyl palmitate, and ii) at least one isoparaffin oil, selected from isodecane, isoundecane, isododecane, isotridecane, isotetradecane, isopentadecane, isohexadecane and isoeicosane, and iii) 0 - no more than 1 wt. % cyclomethicone | 30 to 95 | 40 to 60 | 45 to 55 | 40 to 55 |
| Free water | 0 to 7 | 0 to 7 | 0 to 3 | 0 to 3 |
| Methoxy PEG-22/Dodecyl Glycol Copolymer | 0.01 to 5 | 0.1 to 3 | 0.5 to 2 | 1 to 1.5 |

|  | 41 | 42 | 43 | 44 |
|---|---|---|---|---|
| Antiperspirant aluminum salt (USP) | 5.0 to 40 | 10 to 35 | 15 to 28 | 23 to 27 |
| Triethyl citrate/ester/$C_{10}$-$C_{13}$ isoparaffin | 30 to 95 | 40 to 60 | 45 to 55 | 40 to 55 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |

**wherein $R^1$ is a methyl group,
$R^2$ is an n-decyl group,
m is a rational number from 21 to 23,
n = 0,
p is a rational number from 4 to 8.

|  | 45 | 46 | 47 | 48 |
|---|---|---|---|---|
| Antiperspirant aluminum salt (USP) | 5.0 to 40 | 10 to 35 | 15 to 28 | 23 to 27 |
| Triethyl citrate/ester/$C_{10}$-$C_{13}$ isoparaffin | 30 to 95 | 40 to 60 | 45 to 55 | 40 to 55 |
| Free water | 0 to 7 | 0 to 7 | 0 to 3 | 0 to 3 |
| Methoxy PEG-22/Dodecyl Glycol Copolymer | 0.01 to 5 | 0.1 to 3 | 0.5 to 2 | 1 to 1.5 |

|  | 49 | 50 | 51 | 52 |
|---|---|---|---|---|
| Antiperspirant aluminum salt (USP) | 5.0 to 40 | 10 to 35 | 15 to 28 | 23 to 27 |
| Triethyl citrate/ester/$C_{10}$-$C_{13}$ isoparaffin | 30 to 95 | 40 to 60 | 45 to 55 | 40 to 55 |
| Free water | 0 to 7 | 0 to 7 | 0 to 3 | 0 to 3 |
| ACTIVATOR-(I)** | 0.01 to 5 | 0.1 to 3 | 0.5 to 2 | 1 to 1.5 |
| Cyclomethicone | 0 to 2 | 0 to 2 | 0 to 1 | 0 to 1 |

**wherein $R^1$ is a methyl group,
$R^2$ is an n-decyl group,
m is a rational number from 21 to 23,
n = 0,
p is a rational number from 4 to 8.

|  | 53 | 54 | 55 | 56 |
|---|---|---|---|---|
| Antiperspirant aluminum salt (USP) | 5.0 to 40 | 10 to 35 | 15 to 28 | 23 to 27 |
| Triethyl citrate/ester/$C_{10}$-$C_{13}$ isoparaffin | 30 to 95 | 40 to 60 | 45 to 55 | 40 to 55 |
| Free water | 0 to 7 | 0 to 7 | 0 to 3 | 0 to 3 |
| Methoxy PEG-22/Dodecyl Glycol Copolymer | 0.01 to 5 | 0.1 to 3 | 0.5 to 2 | 1 to 1.5 |
| Cyclomethicone | 0 to 2 | 0 to 2 | 0 to 1 | 0 to 1 |

The present application also provides the use of at least one alkyl-modified polyether of the general formula ACTIVATOR-(I)

ACTIVATOR-(I)

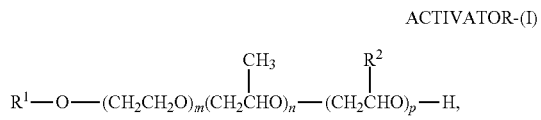

wherein $R^1$ signifies an aliphatic hydrocarbon residue with 1 to 3 C atoms, $R^2$ an aliphatic hydrocarbon residue with 8 to 30 C atoms, m a rational number from 10 to 50, n a rational number from 0 to 10 and p a rational number from 1 to 10, in an antiperspirant composition containing at least one active antiperspirant substance and 0-7 wt. %, preferably 0-3 wt. %, free water, for improving sweat reduction.

"Improving sweat reduction" is to be understood according to the invention as both a reduction of the amount of sweat and an acceleration of the release of the active antiperspirant substance from the composition according to the invention.

The present application also provides the use of at least one alkyl-modified polyether of the general formula ACTIVATOR-(I)

ACTIVATOR-(I)

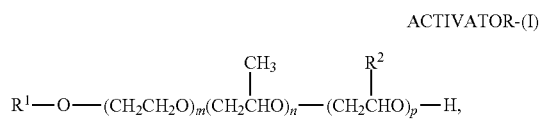

wherein $R^1$ signifies an aliphatic hydrocarbon residue with 1 to 3 C atoms, $R^2$ an aliphatic hydrocarbon residue with 8 to 30 C atoms, m a rational number from 10 to 50, n a rational number from 0 to 10 and p a rational number from 1 to 10, in an antiperspirant composition containing at least one active antiperspirant substance and 0-7 wt. %, preferably 0-3 wt. %, free water, for improving sweat reduction, wherein the alkyl-modified polyether is present in a composition.

The present invention also provides the non-therapeutic, cosmetic use of an antiperspirant composition for reducing and/or regulating perspiration and/or body odor.

With regard to other preferred embodiments of the uses according to the invention, the statements made relating to the compositions according to the invention apply mutatis mutandis.

The present invention also provides a non-therapeutic, cosmetic method of reducing and/or regulating sweat formation and/or body odor, in which a composition according to the invention or a composition that is preferred according to the invention is applied in an effective quantity onto the skin, preferably onto the skin in the arm pit area.

With regard to other preferred embodiments of the method according to the invention, the statements made relating to the compositions according to the invention apply mutatis mutandis.

The following examples are intended to illustrate the invention without limiting it thereto.

Antiperspirant suspension compositions to be made up in the form of a roll-on in a roller ball dispenser (all quantitative data are in wt. %).

| Trade name | INCI | No. 1.1 | No. 1.2 |
|---|---|---|---|
|  | Activated Aluminum Zirconium Pentachlorohydrex - Gly | 22.0 | — |
| Reach AZP 908 | Activated Aluminum Zirconium Tetrachlorohydrex - Gly | — | 24 |
|  | Isopropyl Myristate | 70.6 | 64.8 |
| Elfacos E 200 | Methoxy PEG-22/Dodecyl Glycol Copolymer | 2 | 2 |
| Propylene carbonate | Propylene Carbonate | 0.9 | 1.2 |
| Bentone 38 V CG | Disteardimonium Hectorite | 3.8 | 5 |
| Parfum InCaps | Incapsulated Fragrance | 0.2 | — |
| Parfum | Fragrance | 0.5 | 1 |

TABLE 2

Antiperspirant wax sticks

| | 2.1 | 2.2 | 2.3 | 2.4 | 2.5 | 2.6 | 2.7 |
|---|---|---|---|---|---|---|---|
| PPG-14 butyl ether | 15.00 | 18.00 | 12.00 | 19.00 | 6.00 | 10.50 | 10.50 |
| Hydrogenated castor oil | 1.00 | 1.50 | 2.00 | 1.50 | 1.80 | 3.00 | 3.00 |
| Stearyl alcohol | 20.00 | 18.00 | 15.00 | 18.00 | 17.00 | 23.50 | 23.50 |
| Ceteareth-30 | 3.00 | 2.00 | 4.00 | — | 3.00 | 3.00 | — |
| Isoceteth-20 | — | — | — | 2.50 | — | — | — |
| Elfaeos E 200 | 2.0 | 1.5 | 1.5 | 1.00 | 2.0 | 1.0 | 1.0 |
| Parfum | 1.00 | 1.20 | 0.80 | 1.50 | 1.00 | 1.50 | 1.50 |
| Aluminum chlorohydrate | 20.00 | 22.00 | 18.00 | — | 20.00 | — | — |
| Aluminum zirconium tetrachlorohydrate gly | — | — | — | 22.00 | — | 20.00 | — |
| Aluminum zirconium pentachlorohydrate gly | — | — | — | — | — | — | 20.00 |
| Allantoin | 0.10 | — | — | 0.10 | — | — | — |
| Cocoglycerides (mp 30-32° C.) | 4.00 | 6.00 | 3.00 | 5.00 | 6.00 | — | — |
| Myristyl myristate | — | — | — | — | — | 1.70 | 1.40 |
| Silica | — | — | — | — | — | 0.80 | — |
| Silica dimethyl silylate | — | — | — | — | — | 1.00 | — |
| Talc | 3.00 | 2.00 | 5.00 | 3.00 | 3.00 | — | — |
| Tocopheryl acetate | 0.20 | — | 0.50 | 0.10 | — | — | — |
| Cyclopentasiloxane | to 100 | to 100 | to 100 | to 100 | to 100 | to 100 | to 100 |

Compositions nos. 1.1-2.7 according to the invention were applied onto the skin in the arm pit area.

TABLE 3

Antiperspirant wax sticks

| | 3.1 | 3.2 | 3.3 | 3.4 | 3.5 |
|---|---|---|---|---|---|
| Hexyl decanol | 10.00 | 12.00 | 10.00 | 8.00 | 8.00 |
| PPG-14 butyl ether | 6.00 | 5.00 | 6.00 | 8.00 | 8.00 |
| Hydrogenated castor oil | 4.00 | 5.00 | 6.00 | 5.00 | 5.00 |
| Stearyl alcohol | 12.00 | 14.00 | 11.00 | 16.00 | 16.00 |
| Cetyl alcohol | 6.00 | 5.00 | 6.00 | 3.00 | 3.00 |
| PEG-20 glyceryl stearate | 5.00 | 4.00 | 6.00 | 4.00 | 4.00 |
| Ceteareth-30 | 3.00 | 1.00 | 3.00 | — | — |
| Parfum | 1.00 | 1.20 | 0.80 | 1.00 | 1.00 |
| Aluminum chlorohydrate | 20.00 | 20.00 | 18.00 | — | — |
| Aluminum zirconium tetrachlorohydrate glyc | — | — | — | 23.00 | 23.00 |
| Talc | 8.00 | 5.00 | 8.00 | 7.00 | 7.00 |
| Elfacos E 200 | 2.0 | 1.5 | 1.5 | 1.00 | 2.0 |
| Cyclopentasiloxane | to 100 | to 100 | to 100 | to 100 | to 100 |

TABLE 4

Water-free antiperspirant wax sticks without cyclomethicone

| | 4.1 | 4.2 | 4.3 | 4.4 | 4.5 | 4.6 |
|---|---|---|---|---|---|---|
| Stearyl alcohol | 16 | 18 | 18 | 18 | 18 | 18 |
| Behenyl alcohol | — | — | 0.2 | — | — | — |
| Ceteareth-30 | 3 | 3 | 3 | 3 | 3 | 3 |
| PPG-14 butyl ether | 15 | 5 | 10 | 14.5 | 10 | 7.5 |
| Dimethicone (2 cSt) | — | — | 18.4 | 23 | 22.5 | 23.5 |
| Dimethicone (5 cSt) | 31.5 | 43 | 16.9 | 11 | — | — |
| Elfacos E 200 | 2.0 | 1.5 | 1.5 | 1.00 | 2.0 | 1.5 |
| Hydrogenated polydecene | — | — | — | — | 15 | 15 |
| Cocoglycerides (mp 30-32° C.) | 5 | 4 | 4 | 4 | 4 | 4 |
| Hydrogenated castor oil | 1.5 | 1.5 | 2 | 1.5 | 1.5 | 1.5 |
| Aluminum chlorohydrate | 20 | 20 | 20 | 20 | 20 | 20 |
| Talc | 5 | 3 | 5 | 3 | 3 | 5 |
| Parfum | 1 | 1 | 1 | 1 | 1 | 1 |

Compositions nos. 3.1-4.6 according to the invention were applied onto the skin in the arm pit area.

TABLE 5

Water-free antiperspirant wax sticks with two phases

| First (outer) phase | 5.1 | 5.2 | 5.3 |
|---|---|---|---|
| $C_{12-15}$ Alkyl benzoate | 9.15 | 28.60 | 32.40 |
| Isopropyl myristate | — | — | 15.62 |
| Phenyl trimethicone (DC 556) | — | — | 2.60 |
| 12-Hydroxystearic acid | 12.00 | 12.00 | 6.00 |
| N-lauroyl glutamic acid di-n-butylamide | 2.50 | 2.00 | 1.35 |
| C20-40 Pareth-10 | 3.00 | 3.00 | 3.00 |
| Elfacos E 200 | 2.00 | 1.00 | 1.50 |
| Activated Al—Zr chlorohydrate gly; 17.5 wt. % USP active substance | 33.50 | 33.50 | 33.50 |
| Parfum | 3.85 | 2.50 | 4.03 |
| Parfum (encapsulated) | — | 1.50 | — |
| Cyclomethicone (DC 245) | 34.00 | 16.20 | — |

| Second phase (inner strip or cylinder) | 5.4 | 5.5 | 5.6 |
|---|---|---|---|
| $C_{12-15}$ Alkyl benzoate | 46.55 | 51.02 | 56.08 |
| Isopropyl myristate | — | — | 25.85 |
| Phenyl trimethicone (DC 556) | — | — | 4.30 |
| 12-Hydroxystearic acid | 15.00 | 15.44 | 10.00 |
| N-Lauroyl glutamic acid di-n-butylamide | 1.50 | 1.50 | 2.00 |
| Dye | 0.10 | 0.10 | 0.07 |
| Parfum | 0.85 | 1.24 | 1.70 |
| Cyclomethicone (DC 245) | 36.00 | 30.70 | — |

Water-free antiperspirant wax sticks with two phases were produced with an outer phase 5.1 and an inner phase 5.4, outer phase 5.2 and inner phase 5.5 and with an outer phase 5.3 and inner phase 5.6. Other combinations of outer and inner phase are, of course, also possible.

Compositions nos. 5.1/5.3, 5.2/5.4 and 5.3/5.6 according to the invention were applied onto the skin in the arm pit area.

TABLE 6

Antiperspirant cream, water-free (soft solid)

|  | 6.1 | 6.2 | 6.3 | 6.4 |
|---|---|---|---|---|
| Aluminum chlorohydrate | 20.00 | 22.00 | 20.00 | — |
| Aluminum zirconium tetrachlorohydrate gly | — | — | — | 24.00 |
| Hexyl decanol | 5.00 | 4.50 | 5.50 | 6.00 |
| Dicaprylyl ether | 3.00 | 4.00 | 3.50 | 5.00 |
| Cocoglycerides | 5.00 | 6.00 | 7.00 | 3.00 |
| C18-C36 Triglycerides | 6.00 | 5.00 | 4.00 | 3.00 |
| Ceteareth-30 | 3.00 | 2.00 | 2.50 | 4.00 |
| PEG-20 glyceryl stearate | 5.00 | 6.00 | 3.00 | 2.00 |
| Elfacos E 200 | 2.00 | 2.00 | 1.00 | 1.50 |
| Cellulose | 3.00 | 2.00 | 5.00 | 1.00 |
| Aluminum starch octenylsuccinate | 5.00 | 4.00 | 6.00 | 5.00 |
| Silica | 1.00 | 2.00 | 0.50 | — |
| Talc | 10.00 | 5.00 | 7.00 | 12.00 |
| Allantoin | 0.10 | 0.10 | — | — |
| Parfum | 1.00 | 1.50 | 2.00 | 0.80 |
| Cyclopentasiloxane | to 100 | to 100 | to 100 | to 100 |

TABLE 7

Powder (Deodorant/antiperspirant)

|  | 7.1 | 7.2 | 7.3 | 7.4 |
|---|---|---|---|---|
| Aluminum chlorohydrate | 20.00 | — | — | — |
| Aluminum zirconium tetrachlorohydrate gly | — | — | — | 24.00 |
| Silica | 2.00 | 2.00 | 1.00 | 1.00 |
| Triclosan | — | 0.30 | 0.10 | — |
| Sensiva SC 50 | — | — | 1.00 | — |
| Parfum | 1.00 | 0.50 | 2.00 | 1.00 |
| Parfum (incapsulated) | — | 1.00 | — | 1.00 |
| Menthyl lactate (incapsulated) | — | — | 1.00 | 1.00 |
| Elfacos E 200 | 2.00 | 2.00 | 1.00 | 1.50 |
| Talc | to 100 | to 100 | to 100 | to 100 |

The powder examples 7.1-7.4 can be made up both as loose powder and as pressed powder. Compositions nos. 6.1-7.4 according to the invention were applied onto the skin in the arm pit area.

TABLE 8

Dibenzylidene sorbitol-based antiperspirant gel sticks

|  | 8.1 | 8.2 | 8.3 | 8.4 (deodorant) |
|---|---|---|---|---|
| Al/Zr tetrachlorohydrate gly | 11 | 11 | 11 | 3 |
| Dibenzylidene sorbitol | 1 | 1.3 | 1.1 | 1.3 |
| Hydroxypropyl cellulose | 0.3 | 0.3 | 0.35 | 0.5 |
| Na$_4$EDTA | 0.2 | 0.2 | 0.2 | 0.2 |
| Diisopropyl sebacate | — | 1 | 1 | — |
| Glycereth-7 diisononanoate | 0.5 | — | — | — |
| Oleth-10 | — | — | — | 0.75 |
| PPG-10 butanediol | — | — | — | 0.75 |
| PPG-3 myristyl ether | — | — | — | 0.75 |
| Elfacos E 200 | 1.00 | 1.00 | 1.00 | 1.00 |
| Parfum | 1.25 | 1.25 | 1.25 | 1.25 |
| 1,2-Propylene glycol | to 100 | to 100 | to 100 | to 100 |

TABLE 9

Water-free roll-on compositions

|  | 9.1 | 9.2 | 9.3 | 9.4 | 9.5 |
|---|---|---|---|---|---|
| Quaternium-18 hectorite | 4.0 | 2.5 | 2.5 | 3.2 | 3.6 |
| Parfum | 0.5 | 0.5 | 0.5 | 1.0 | 1.0 |

TABLE 9-continued

Water-free roll-on compositions

|  | 9.1 | 9.2 | 9.3 | 9.4 | 9.5 |
|---|---|---|---|---|---|
| Parfum (incapsulated) | 0.5 | 0.5 | 0.5 | 1.0 | 1.0 |
| Al/Zr tetrachlorohydrate gly (activated) | 20 | 20 | 20 | — | — |
| Al/Zr pentachlorohydrate gly (activated) | — | — | — | 20 | 20 |
| Elfacos E 200 | 1.00 | 1.00 | 1.00 | 1.00 | 2.00 |
| Propylene carbonate | 1.0 | 1.0 | — | — | 1.0 |
| Aerosil 300 (fumed silica) | — | 0.2 | 0.4 | — | — |
| Isopropyl myristate | to 100 | to 100 | to 100 | to 100 | to 100 |

The compositions nos. 8.1-9.5 according to the invention were applied onto the skin in the arm pit area.

The removal of the compositions according to the invention (for example by washing) takes place in the context of the usual hygiene routine, for example 1, 2, 3, 4, 5, 6, 7, 8, 9, 10, 11, 12 or 24 hours after application.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An antiperspirant composition for personal body care, made up as a non-aerosol, stick, soft solid, cream, gel, non-sprayable suspension, non-sprayable solution or impregnated on a substrate, comprising:
   a) at least one active antiperspirant substance;
   b) at least one oil which is liquid under normal conditions as carrier;
   c) 0-7 wt. % free water, based on the weight of the composition; and
   d) an active antiperspirant substance release agent at a concentration of from 1 to 2 wt. % and having a hydrophilic-lipophilic balance (HLB) value in the range of 5 to 7, the active antiperspirant release agent comprising at least one alkyl-modified polyether of the general formula ACTIVATOR-(I):

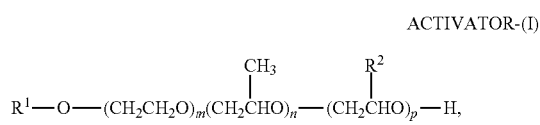

ACTIVATOR-(I)

$$R^1-O-(CH_2CH_2O)_m(CH_2CHO)_n-(CH_2CHO)_p-H,$$
$$\phantom{R^1-O-(CH_2CH_2O)_m(}CH_3\phantom{)_n-(}R^2$$

wherein $R^1$ signifies an aliphatic hydrocarbon residue with 1 to 3 C atoms,
$R^2$ signifies an aliphatic hydrocarbon residue with 8 to 30 C atoms,
m is a rational number from 10 to 50,
n is a rational number from 0 to 10,
p is a rational number from 1 to 10.

2. The composition according to claim 1, wherein the alkyl-modified polyether d) is selected from compounds of the general formula ACTIVATOR-(I), wherein $R^1$ is selected from a methyl group, an ethyl group, an n-propyl group and a 1-methylethyl group, preferably a methyl group, $R^2$ is selected from an n-octyl, 2-ethylhexyl, n-nonyl, n-decyl, 2-ethyloctyl, n-undecyl, n-dodecyl, 2-ethyldecyl, n-tridecyl, myristyl, n-pentadecyl, cetyl, palmityl, stearyl, elaidyl, arachidyl, behenyl or cocyl group, preferably an n-decyl group, m represents a number from 12-30, preferably 22, n represents a rational number from 0-8, preferably 0-4, particularly preferably 0, p represents a rational number from 1-9, preferably 4-8, particularly preferably 5-7.

3. The composition according to claim 1, wherein at least one alkyl-modified polyether of the general formula ACTIVATOR-(I) has an HLB value in the range of 5-7, and wherein $R^1$=methyl, $R^2$=n-decyl, m=22, n=0 and p=4-5.

4. The composition according to claim 1, wherein at least one alkyl-modified polyether of the general formula ACTIVATOR-(I) has an HLB value in the range of 5-7, and wherein $R^1$=methyl, $R^2$=n-decyl, m=22, n=0 and p=7-8.

5. The composition according to claim 1, wherein the alkyl-modified polyether d) of the general formula ACTIVATOR-(I) is selected from compounds with the INCI name Methoxy PEG-22/Dodecyl Glycol Copolymer.

6. The composition according to claim 1, wherein the at least one carrier oil b) which is liquid under normal conditions is selected from the group consisting of volatile cyclic or linear silicone oils, non-volatile higher molecular-weight linear dimethyl polysiloxanes, esters of linear or branched saturated or unsaturated fatty alcohols having 2-30 carbon atoms with linear or branched saturated or unsaturated fatty acids having 2-30 carbon atoms, which may be hydroxylated, benzoic acid esters of linear or branched $C_{8-22}$ alkanols, $C_8$-$C_{22}$ fatty alcohol esters of monohydric or polyhydric $C_2$-$C_7$ hydroxycarboxylic acids, the addition products of ethylene oxide and/or propylene oxide to monohydric or polyhydric $C_{3-20}$ alkanols, liquid paraffin oils, isoparaffin oils, in particular isodecane, isoundecane, isododecane, isotridecane, isotetradecane, isopentadecane, isohexadecane and isoeicosane, synthetic hydrocarbons, such as polyisobutene or polydecene, and alicyclic hydrocarbons, branched saturated or unsaturated fatty alcohols with 6-30 carbon atoms, mixtures of Guerbet alcohols and Guerbet alcohol esters, the symmetrical, asymmetrical or cyclic esters of carbonic acid with fatty alcohols, triglycerides of linear or branched, saturated or unsaturated, optionally hydroxylated $C_{8-30}$ fatty acids, dicarboxylic acid esters of linear or branched $C_2$-$C_{10}$ alkanols, di-n-alkyl ethers with a total of 12 to 36 C atoms, and mixtures thereof.

7. The composition according to claim 1, wherein the at least one carrier oil b) which is liquid under normal conditions comprises at least one isoparaffin oil selected from the group consisting of isodecane, isoundecane, isododecane, isotridecane, isotetradecane, isopentadecane, isohexadecane and isoeicosane.

8. The composition according claim 1, comprising from 0 to no more than 1 wt. % of cyclomethicones.

9. The composition according to claim 1, wherein the carrier oil b) which is liquid under normal conditions consists of a mixture of b)i) an ester oil, selected from 2-ethylhexyl palmitate, isopropyl myristate and isopropyl palmitate, and b)ii) at least one isoparaffin oil, selected from isodecane, isoundecane, isododecane, isotridecane, isotetradecane, isopentadecane, isohexadecane and isoeicosane, and b)iii) 0 to no more than 1 wt. % of cyclomethicones.

10. A non-therapeutic, cosmetic method of reducing and/or regulating sweat formation and/or body odor, in which a composition according to the invention of claim 1, is applied in an effective quantity onto the skin in the arm pit area.

* * * * *